United States Patent [19]

Costantini et al.

[11] Patent Number: 5,670,465
[45] Date of Patent: Sep. 23, 1997

[54] PREPARATION OF P-FUCHSONES AND SYNTHESIS OF P-DIHYDROXYLATED AROMATIC COMPOUNDS THEREFROM

[75] Inventors: Michel Costantini, Lyons; Daniel Manaut, Meyzieu; Daniel Michelet, Saint-nom-la-Breteche, all of France

[73] Assignee: Rhone-Poulenc Chimie, Courbevoie Cedex, France

[21] Appl. No.: 464,311

[22] Filed: Jun. 5, 1995

Related U.S. Application Data

[62] Division of Ser. No. 179,234, Jan. 10, 1994, Pat. No. 5,460,839.

[30] Foreign Application Priority Data

| Jan. 8, 1993 | [FR] | France | 93 00119 |
| Jan. 8, 1993 | [FR] | France | 93 00120 |
| Jan. 8, 1993 | [FR] | France | 93 00121 |
| Sep. 22, 1993 | [FR] | France | 93 11262 |

[51] Int. Cl.$^6$ .................................................. C07C 37/60
[52] U.S. Cl. ........................... 568/771; 568/741; 568/803
[58] Field of Search .................................. 568/771, 741, 568/803

[56] References Cited

U.S. PATENT DOCUMENTS

| 2,841,623 | 7/1958 | Norton et al. | 552/304 |
| 3,649,653 | 3/1972 | Becker | 568/304 |
| 4,081,485 | 3/1978 | Eguchi | 552/304 |
| 4,909,960 | 3/1990 | Kung et al. | 568/305 |
| 5,414,155 | 5/1995 | Costantini et al. | 568/771 |

FOREIGN PATENT DOCUMENTS

| 0397553 | 11/1990 | European Pat. Off. |
| 0480800 | 4/1992 | European Pat. Off. |
| 2071464 | 7/1971 | France |
| 2071464 | 9/1971 | France |
| 2266683 | 10/1975 | France |
| 2336364 | 7/1977 | France |
| 2563446 | 10/1985 | France |
| 2677598 | 4/1992 | France |

OTHER PUBLICATIONS

Chemical Abstracts, vol. 113, No. 3, 16 Juillet 1990, Columbus, Ohio, US; abstract no. 23364n, p. 606, colonne 2; & JP–A–2 078 641 (Mitsui Petrochemical Industries).

Collection of Czechoslovak Chemical Communications, vol. 46, 1981, Prague CS, pp. 873–882, J. Velek et al, "IR Spectra of Some Quinone Methides. A Study of the ortho–Effect".

Chemical Abstracts, vol. 108, 1988, Columbus, Ohio, US; abstract no. 150241s, Kozlikovskii, YA.B. et al, "Reaction of phenol with benzophenone in the presence of aluminum phenolate.", p. 723; colonne 1; & IZV. Vyssh. Uchebn. Zaved., Khim. Khim Tekhnol., vol. 30, No. 7, 1987, pp. 31–34.

Methoden der Organischen Chimie (Houben–1 WEYL), vol. VII, No. 3B, 1979, Stuttgart, pp. 458–462., P. Grunanger "Chinonmethide", pp. 459–460.

Primary Examiner—James H. Reamer
Attorney, Agent, or Firm—Burns, Doane, Swecker & Mathis, L.L.P.

[57] ABSTRACT p-Dihydroxylated aromatic compounds are prepared via the oxidation of p-fuchsones, the latter advantageously being synthesized by reacting a phenolic compound having at least one hydrogen atom in the para-position to the hydroxyl function with a non-enolizable ketonic compound, in the presence of a catalytically effective amount of an acid catalyst and, optionally, a cocatalytically effective amount of an ionizable sulfur-containing compound.

22 Claims, 1 Drawing Sheet

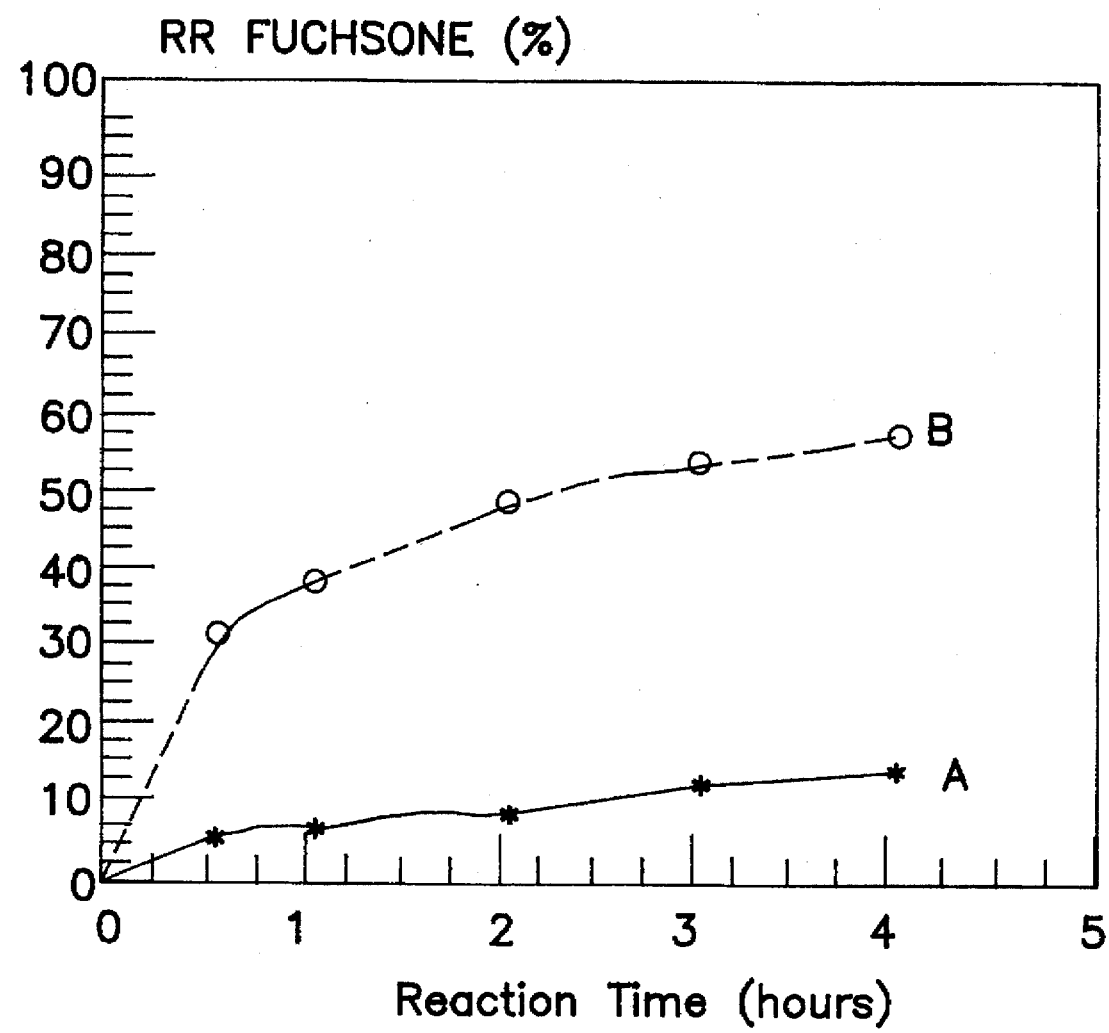

PREPARATION OF P-FUCHSONES AND SYNTHESIS OF P-DIHYDROXYLATED AROMATIC COMPOUNDS THEREFROM

This application is a divisional, of application Ser. No. 08/179,234, filed Jan. 10, 1994 now U.S. Pat. No. 5,466,839.

CROSS-REFERENCE TO COMPANION APPLICATION

Our application Ser. No. 179,130, now U.S. Pat. No. 5,414,155, filed concurrently herewith and assigned to the assignee hereof.

BACKGROUND OF THE INVENTION

1. Field of the Invention

The present invention relates to the preparation of p-fuchsones and also to the synthesis of p-dihydroxylated aromatic compounds from p-fuchsone reagents, in particular from the p-fuchsones thus prepared.

2. Description of the Prior Art

There are scant references in the literature describing the synthesis of fuchsones. Typically, their preparation is based on the dehydration of a carbinol.

Thus, I. S. Ioffe et al, *J. Gen. Chem. USSR*, 19, pages 917–28 (1949), describes the preparation of 4-hydroxy triphenyl carbinol by reacting $Ph_2CCl_2$ with molten phenol.

H. Burton et al, *J. Chem. Soc.*, 3089–3090 (1955), describes the synthesis of 4-hydroxy triphenyl carbinol via the addition of $Ph_2CCl_2$ to a suspension of aluminum chloride in carbon disulfide and then introducing into that reaction medium phenol in solution in carbon disulfide.

The 4-hydroxy triphenyl carbinol thus obtained is then dehydrated. One dehydration technique described by I. S. Ioffe et al, supra, comprises heat-treating the carbinol after the addition of acetic acid thereto, thus providing the following fuchsone:

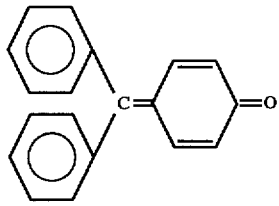

Notable disadvantages presented by the processes heretofore known to this art include the reality that it is virtually impossible to carry out same on an industrial scale by virtue of a raw material which is difficult to obtain ($Ph_2CCl_2$) and the difficulty in handling reactants such as aluminum chloride and carbon disulfide.

SUMMARY OF THE INVENTION

Accordingly, a major object of the present invention is the provision of an improved process for the preparation of p-fuchsones that can be carried out on an industrial scale, with good reaction yields.

Another object of the invention is the synthesis of p-dihydroxylated aromatic compounds from the p-fuchsones, in particular from the p-fuchsones thus prepared.

Briefly, the present invention features a process for the preparation of a p-fuchsone, comprising reacting a phenolic compound having a hydrogen atom in the para-position to the hydroxyl group with a non-enolizable ketonic compound, in the presence of a catalytically effective amount of an acid and, optionally, in the presence of an effective amount of an ionizable sulfur-containing compound.

DETAILED DESCRIPTION OF BEST MODE AND PREFERRED EMBODIMENTS OF THE INVENTION

More particularly according to the present invention, by the term "p-fuchsone" is intended any chemical compound comprising the following 1,4-methylene quinone structural unit:

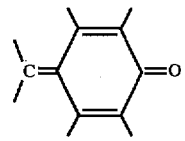

The starting substrate is an aromatic compound bearing at least one hydroxyl group and having a hydrogen atom in the para-position to said hydroxyl group. The term "aromatic compound" is used to connote the conventional definition of aromaticity, as described, in particular, in Jerry March, *Advanced Organic Chemistry*, 3rd edition, pp. 37 et seq, John Wiley and Sons (1985).

By the term "non-enolizable ketonic compound" is intended a ketone having two tertiary carbon atoms in the α-position to the carbonyl group.

By the term "ionizable sulfur-containing compound" is intended any sulfur-containing compound which ionizes in the presence of water to provide an ion having a free valence on the sulfur atom.

In one embodiment of the invention, the subject process is carried out in the presence of an additive, namely, an ionizable sulfur-containing compound. Indeed, it has now been determined that carrying out the process in the presence of such sulfur-containing compound increases the reaction kinetics. Thus, it was found that the rate of formation of the fuchsone was considerably increased and could be multiplied by a factor of ten or even more.

The present invention also features a process for the preparation of a p-dihydroxylated aromatic compound, comprising reacting an oxidizing agent with a p-fuchsone.

In a preferred embodiment of the invention, a p-fuchsone prepared as described above is used for the synthesis of the p-dihydroxylated aromatic compound.

The present invention also features the preparation of a p-dihydroxylated aromatic compound by reacting a phenolic compound having a hydrogen atom in the para-position to the hydroxyl group with a non-enolizable ketonic compound, in the presence of an effective amount of an acid and, optionally, in the presence of an effective amount of an ionizable sulfur-containing compound, and then oxidizing the p-fuchsone thus obtained, without separation of the latter.

The present invention also features a process for the preparation of a p-hydroxylated aromatic compound, comprising oxidizing a phenolic compound starting material in the presence of an effective amount of a p-fuchsone.

In accordance with the present invention, a p-fuchsone is prepared by reacting the phenolic and ketonic compounds, as described above, in the presence of an acid and, optionally, an ionizable sulfur-containing compound.

The process of this invention is more particularly applicable to the phenolic compounds having the following general formula (I):

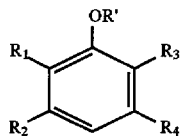  (I)

in which formula (I) the position para to the oxygen moiety is free; the radicals $R_1$, $R_2$, $R_3$ and $R_4$, which may be identical or different, are each a hydrogen atom or any "inert" substituent, with the proviso that the radicals $R_1$ and $R_2$ and/or $R_3$ and $R_4$ which are borne by adjacent carbon atoms may together form, with the carbon atoms from which they depend, a ring member; and R' is a hydrogen atom or a hydrocarbon radical having from 1 to 24 carbon atoms, which can be a branched or straight chain, saturated or unsaturated acyclic aliphatic radical, a monocyclic or polycyclic, saturated or unsaturated cycloaliphatic radical, or a branched or straight chain, saturated or unsaturated aliphatic radical bearing a cyclic substituent.

By the term "cyclic substituent" is intended a saturated, unsaturated or aromatic carbocycle advantageously having from 4 to 7 carbon atoms and preferably 6 carbon atoms.

The process of the invention is applicable to any phenolic compound corresponding to general formula (I) and, more particularly, the phenolic compounds of formula (I) in which R' is a hydrogen atom, a branched or straight chain alkyl radical having from 1 to 6 carbon atoms, preferably from 1 to 4 carbon atoms, and more particularly a methyl or ethyl radical, a cyclohexyl radical, or a benzyl radical.

The phenolic compound of formula (I) can be substituted by one or more substituents $R_1$, $R_2$, $R_3$ and $R_4$. Exemplary such substituents are set forth hereinbelow, for purposes of illustration only. Any substituent may be present on the ring nucleus as long as it does not interfere with the preparation of the desired final product, i.e., is "inert."

The process of the invention is more preferably applicable to phenolic compounds of formula (I) in which $R_1$, $R_2$, $R_3$ and $R_4$, which may be identical or different, are each a radical $R_0$, i.e., either a hydrogen atom; a branched or straight chain alkyl radical having from 1 to 6 carbon atoms, preferably from 1 to 4 carbon atoms, such as methyl, ethyl, propyl, isopropyl, butyl, sec-butyl and tert-butyl; a branched or straight chain alkenyl radical having from 2 to 6 carbon atoms, preferably from 2 to 4 carbon atoms, such as vinyl or allyl; a branched or straight chain alkoxy radical having from 1 to 6 carbon atoms, preferably from 1 to 4 carbon atoms, such as methoxy, ethoxy, propoxy, isopropoxy and butoxy; an acyl group having from 2 to 6 carbon atoms; or a radical of the following formulae:

—$R_5$—OH

—$R_5$—COO$R_6$

—$R_5$—X

—$R_5$—CF$_3$ in which formulae $R_5$ is a valence bond or a saturated or unsaturated, branched or straight chain divalent hydrocarbon radical having from 1 to 6 carbon atoms, such as, for example, methylene, ethylene, propylene, isopropylene or isopropylidene, $R_6$ is a hydrogen atom or a branched or straight chain alkyl radical having from 1 to 6 carbon atoms, and X is a halogen atom, preferably an atom of chlorine, bromine or fluorine; or at least one of the radicals $R_1$, $R_2$, $R_3$ and $R_4$, which may be identical or different, is a radical $R_7$, i.e., a saturated or unsaturated carbocyclic radical having from 4 to 7 carbon atoms, preferably a cyclohexyl radical; a radical of the formula:

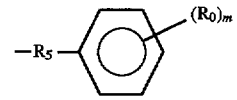

in which $R_5$ is a valence bond or a saturated or unsaturated, branched or straight chain divalent hydrocarbon radical having from 1 to 6 carbon atoms, such as, for example, methylene, ethylene, propylene, isopropylene or isopropylidene, $R_0$ is as defined above, and $\underline{m}$ is an integer ranging from 0 to 4; a radical —$R_5$—A—$R_8$ in which $R_5$ is as defined above, $R_8$ is a branched or straight chain alkyl radical having from 1 to 6 carbon atoms, or a radical of the formula:

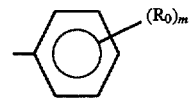

and A is one of the following groups:

$$-O-, \quad -COO-, \quad -OCOO-, \quad -SO_2-, \quad -CO-N- \atop R_9$$

in which formulae $R_9$ is a hydrogen atom or an alkyl radical having from 1 to 4 carbon atoms, or a cyclohexyl or phenyl radical, with the proviso that the radicals $R_1$ and $R_2$ and/or $R_3$ and $R_4$ borne by adjacent carbon atoms may together form, with the carbon atoms from which they depend, an unsaturated or aromatic carbocycle having from 4 to 7 carbon atoms and preferably 6 carbon atoms.

Among the compounds of formula (I), preferred are those in which R' is a hydrogen atom; and $R_1$, $R_2$, $R_3$ and $R_4$, which may be identical or different, are each a hydrogen atom, a branched or straight chain alkyl radical having from 1 to 4 carbon atoms, a branched or straight chain alkoxy radical having from 1 to 4 carbon atoms, a hydroxyl group, a halogen atom, a —CF$_3$ group, a cyclohexyl radical, or a phenyl radical, with the proviso that the radicals $R_1$ and $R_2$ and/or $R_3$ and $R_4$ which are borne by adjacent carbon atoms may together form, with the carbon atoms from which they depend, a benzene ring.

More preferred are the compounds of formula (I) in which R' is a hydrogen atom and one of the radicals $R_1$, $R_2$, $R_3$ and $R_4$ is a hydroxyl group, a methyl radical or a methoxy radical and the other three are hydrogen atoms.

Exemplary phenolic compounds of formula (I) which are suitable starting materials for the process of the invention, the following are particularly representative:

(i) those corresponding to formula (I) in which $R_1$, $R_2$, $R_3$ and $R_4$ represent a hydrogen atom, such as phenol or anisole, (ii) those corresponding to formula (I) with a substituent on the benzene ring, such as orthocresol, metacresol, 2-methoxyphenol, 2-enhylphenol, 3-ethylphenol, 2-propylphenol, 2-sec-butylphenol, 2-tert-butylphenol, 3-tert-butylphenol, 2-methoxyphenol, 3-methoxyphenol, methyl salicylate, 2-chlorophenol and 3-chlorophenol, (iii) those corresponding to formula (I) with two substituents on the benzene ring, such as 2,3-dimethylphenol, 2,5-dimethylphenol, 2,6-dimethylphenol, 3,5-dimethylphenol, 2,3-dichlorophenol, 2,5-dichlorophenol, 2,6-dichlorophenol, 3,5-dichlorophenol, 2,6-ditert-butylphenol and 3,5-ditert-butylphenol, (iv) those corresponding to formula (I) with three substituents on the benzene ring, such as 2,3,5-trimethylphenol, 2,3,6-trimethylphenol, 2,3,5-trichlorophenol and 2,3,6-trichlorophenol, (v) those corresponding to formula (I) in which $R_1$ and $R_2$ form a benzene ring, such as 1-hydroxynaphthalene, and (vi) those corresponding to formula (I) in which $R_1$ is a radical of type $R_7$, such as 2-phenoxyphenol and 3-phenoxyphenol.

Among the phenolic compounds of formula (I), particularly advantageous are phenol, orthocresol and metacresol.

As indicated above, the ketonic compound employed in the process of the invention is characterized in that it is a non-enolizable ketone.

It preferably has the following formula (II):

$$R_a - \underset{\underset{O}{\|}}{C} - R_b \quad \text{(II)}$$

in which $R_a$ and $R_b$, which may be identical or different, are each a hydrocarbon radical having from 3 to 30 carbon atoms, and the carbon atoms of each radical $R_a$ and $R_b$ in position α with respect to the carbonyl group are tertiary carbon atoms.

Exemplary radicals $R_a$ and $R_b$ which are suitable according to the present invention include the branched chain alkyl radicals having at least 3 carbon atoms and aryl radicals having at least 6 carbon atoms, and more particularly tert-butyl, tert-pentyl, tert-hexyl and phenol radicals, and the optionally substituted such radicals.

Preferred ketonic compounds have the following general formula (IIa):

in which $R_{a1}$, $R_{a2}$ and $R_{a3}$ and $R_{b1}$, $R_{b2}$ and $R_{b3}$, which may be identical or different, are each a branched or straight chain alkyl radical having from 1 to 10 carbon atoms, or a cyclohexyl, phenyl or naphthyl radical or optionally substituted such radicals, or $R_{a1}$, $R_{a2}$ and $R_{a3}$ and/or $R_{b1}$, $R_{b2}$ and $R_{b3}$ may together form, with the carbon atom from which they depend, a benzene or naphthalene ring which may optionally be substituted.

Among the ketonic compounds which correspond to formula (IIa), more particularly preferred are ketonic compounds having the following formula (IIb):

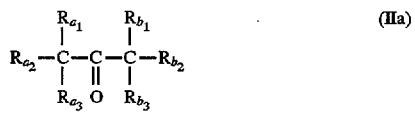

in which $R_c$ and $R_d$, which may be identical or different, are each a hydrogen atom or a substituent, preferably an electron-donor group, and $n_1$ and n2, which may be identical or different, are each a number equal to 0, 1, 2 or 3.

Each "substituent" is selected such that it does not react under the acid conditions of invention. Each is preferably an electron-donor group.

By the term "electron-donor group" is intended a group as defined by H. C. Brown in the Jerry March text, *Advanced Organic Chemistry*, chapter 9, pages 243 and 244 (1985).

Exemplary of these substituents are branched or straight chain alkyl radicals having from 1 to 4 carbon atoms; the phenyl radical; the alkoxy $R_{10}$—O radicals in which $R_{10}$ is a branched or straight chain alkyl radical having from 1 to 4 carbon atoms or the phenyl radical; the hydroxyl group, and the fluorine atom.

More particularly preferred ketonic compounds corresponding to the general formula (IIb) are those in which $R_c$ and $R_d$, which may be identical or different, are each a hydrogen atom or a substituent as described above, preferably in position 4,4' and $n_1$ and $n_2$, which may be identical or different, are each equal to 0 or 1.

Even more preferred ketonic compounds which correspond to the formula (IIb) are those in which $R_c$ and $R_d$, which may be identical or different, are each a hydrogen atom; a methyl, ethyl, tert-butyl or phenyl radical; a methoxy or ethoxy radical; or a hydroxyl group, preferably in position 3,3' and 4,4'.

Specific examples of ketones which can be employed in the process of the invention include the following:

Benzophenone,
2-Methylbenzophenone,
2,4-Dimethylbenzophenone,
4,4'-Dimethylbenzophenone,
2,2'-Dimethylbenzophenone,
4,4'-Dimethoxybenzophenone,
4-Hydroxybenzophenone,
4,4'-Dihydroxybenzophenone,
4-Benzoyldiphenyl.

In accordance with the process of invention, the phenolic compound of formula (I) is reacted with the ketonic compound of general formula (II) in the presence of an acid catalyst.

The catalyst which is suitable for invention is selected such that it has an acidity ranging from 5 to 20, preferably from 10 to 15.

The catalyst used in the process of the invention is an acid catalyst. It may be a homogeneous or a heterogenous catalyst.

It is permissible to use a strong protonic acid and/or a Lewis acid. Exemplary of such strong acids are the halogenated acids, such as hydrochloric acid, hydrobromic acid, hydrofluoric acid, oxyacids which either may or may not be halogenated, such as sulfuric acid, pyrosulfuric acid, perchloric acid, halosulfonic acids, such as fluorosulfonic acid, chlorosulfonic acid or trifluoromethanesulfonic acid, methanesulfonic acid, ethanesulfonic acid, ethanedisulfonic acid, benzenesulfonic acid, benzenedisulfonic acids, toluenesulfonic acids, naphthalenesulfonic acids and naphthalenedisulfonic acids.

Among such acids, preferred are hydrofluoric acid, perchloric acid, trifluoromethanesulfonic acid, paratoluenesulfonic acid, chlorosulfonic acid, fluorosulfonic acid, methanesulfonic acid and benzenesulfonic acid.

Hydrofluoric acid, perchloric acid, trifluoromethanesulfonic acid and ethanesulfonic acid are more particularly preferred.

Other examples of protonic acid catalysts include the sulfonic resins.

Thus, commercially available sulfonic resins can be used, marketed under a variety of tradenames and trademarks, including TEMEX 50, AMBERLYST 15, AMBERLYST 35, AMBERLYST 6 and DOWEX 50W.

The aforesaid resins which are suitable for the present invention comprise a polystyrene skeleton or backbone bearing functional groups which are sulfonic in nature.

The polystyrene skeleton is obtained by polymerization of styrene and divinyl benzene, under the influence of an activation catalyst, in most instances an organic peroxide, which results in a crosslinked polystyrene. The polymerization is typically carried out in suspension and beads or granules of polymer are obtained. They are treated with concentrated sulfuric or sulfochloric acid. A sulfonated styrene divinyl benzene copolymer is thus produced.

Sulfonic resins can also be used which are phenol/formol copolymers, the aromatic nuclei of which bear a methylene sulfonic group. Exemplary of such resins are those commercially available under the trademark DUOLITE ARC 9359.

Other commercially available resins include the perfluorinated resins bearing sulfonic groups and more particularly NAFION which has the general structural formula:

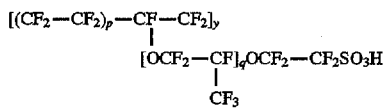

in which $q$ is an integer equal to 1, 2, 3, etc., $p$ ranges from 5 to 13.5 and $y$ is equal to about 1000.

NAFION is prepared from a copolymer of tetrafluoroethylene and perfluoro-[2-(fluorosulfonylethoxy)-propyl] vinyl ether.

These resins may be of the gel type, or of the macro-crosslinked type. They are used in their acid form.

Numerous such resins are commercially available in dry or wet form. One or the other of the forms may be used in the process of the invention.

They are usually in the form of substantially spherical particles having a diameter ranging from 0.3 to 1.5 mm, preferably from 0.5 to 1.2 mm.

Said resins are preferably employed in the process of the invention and more preferably those resins comprising a polystyrene skeleton. However, it is also within the scope of the invention to use resins having a skeleton of another nature just as long as it bears suitable sulfonic groups.

The proportion of sulfonic groups with respect to the polymeric backbone may vary widely and account will be taken thereof when determining the amount of polymer to be used.

The concentration in respect of acid sites of the sulfonic polymer advantageously ranges from 1 to 10 milliequivalent of ions $H^+$ per gram of dry polymer and preferably from 2 to 7 milliequivalent of ions $H^+$ per gram of dry polymer.

The acid forms of mixed oxides, clays and zeolites are tantamount to strong protonic acids.

Exemplary such catalysts having acid properties include, more particularly, combinations of metallic and metalloidic oxides, for example silica/alumina, silica/$Ga_2O_3$ and silica/$B_2O_3$.

Another type of acid mineral catalyst completely suitable for carrying out the process of the invention are the acid clays.

To prepare acid clays, the starting material employed is preferably a natural clay having a structure referred to as "TOT" or tetrahedral/octahedral/tetrahedral.

The TOT clays are in the form of elementary sheets or flakes comprising two layers of tetrahedrons of oxygen atoms including the silicon atoms, separated by a layer of octahedrons of oxygen atoms including the metal M of type $MO_4(OH)_2$ in which M is a divalent or trivalent cation.

When all the tetrahedrons are occupied by ions $Si^{4+}$, the electrical neutrality of the lamina can be measured in two ways, depending on the charge of the octahedral cation:

(1) if it is divalent ($Mg^{2+}$, $Fe^{2+}$, etc. ) all of the octahedral cavities are occupied; the leaf is then referred to as trioctahedral; and (2) if it is trivalent ($Al^{3+}$, $Fe^{3+}$, etc.), two octahedral cavities out of three are occupied and the leaf is dioctahedral.

However, numerous substitutions are possible, both in the tetrahedral layer and in the octahedral layer. They may give rise to a charge deficit of the lamina and neutrality of the crystal is then attained by the insertion of compensating cations between the layers.

The following three classes exist among the TOT clays: smectites, vermiculites and micas.

Among the clays, the class which is the preferred according to the invention is that of the smectites.

Smectites are classified according to the nature of the metal M (aluminum, magnesium, iron, and lithium), the nature of the compensating cation (sodium, potassium and calcium) and the nature of the tetrahedral or octahedral substitution.

The following, among the smectites, are particularly representative:

(a) montmorillonites of the formula $Si_4(Al_{2-y}Mg_y)O_{10}(OH)_2$, $M^+_y$ (b) beidellites of the formula $Si_{4-x}Al_x) Al_2O_{10}(OH)_2$, $M^+_x$ (c) nontronites of the formula $Si_{4-x}Al_x) Fe_2O_{10}(OH)_2$, $M^+_x$ (d) hectorites of the formula $Si_4(Mg_{3-y}Li_y) O_{10}(OH)_2$, $M^+_y$ (e) stevensites of the formula $Si_4(Mg_{3-y}) O_{10}(OH)_2$, $M^+_{2y}$ (f) saponites of the formula $Si_{4-x}Al_x) Mg_3O_{10}(OH)_2$, $M^+_x$ It is even more particularly preferred in accordance with the present invention to use the montmorillonites.

Commercially available clays which are already acid can also be used, such as, in particular, the following clays: KSF, TONSIL OPTIMUM FF and K 10 which are marketed by Süd Chemie.

It is also possible to treat the commercial clays, which either may or may not already be acid, with an aqueous solution of an acid. The concentration of the aqueous solution in respect of acid is variable; however, it will have to have a pH of greater than or equal to 2, such as not to destroy the clay, and it will have to contain an amount of ions $H^+$ expressed in milliequivalent corresponding to at least the exchange capacity of the clay. The exchange capacity of a clay is defined as the number of monovalent cations, expressed in milliequivalent, that 1 g of sample can exchange.

That exchange capacity (or charge per half-mesh) varies for smectites from 0.2 to 0.6 and for vermiculites from 0.6 to 0.9. It is therefore preferable according to the invention to use an acid solution containing as many equivalents $H^+$ as there will be cations to exchange in the clay, therefore containing at least 0.6 and preferably at least 1 milliequivalent acid for 1 g of clay.

To enhance the exchange surface area of the clay, it is optionally possible to then treat it with an alcohol such as methanol, and then dry it.

Clays of the bridged type are also suitable for carrying out the process of the invention.

By the term "bridged clay" are intended clays, between the laminae of which have been introduced bridges or pillars which maintain a basal spacing. The basal spacing (or interlayer distance) is the sum of the thickness of a lamina of the clay and the interlayer spacing.

Exemplary mineral species creating pillars or bridges include those derived from the following elements: aluminum, nickel, cobalt, vanadium molybdenum, rhenium, iron, copper, ruthenium, chromium, lanthanum, cerium, titanium, boron, gallium, zirconium, niobium, tantalum and silicon.

The bridged clays preferably used in the process of the invention are clays which are bridged by pillars of an oxide of aluminum, zirconium, chromium, silicon and cerium.

Such clays are prepared via techniques known in the art.

For the preparation of aluminum-bridged clays, see, inter alia, FR-A-2,563,446 and FR-A-2,656,298; for the preparation of titanium-bridged clays, see FR-A-2,669,016; and for the preparation of cerium-bridged clays, see published French patent application No. 91/04,409.

Among the bridged clays, more particularly preferred are the clays of smectite type. Among such smectites, representative are the heidellites, in particular synthetic heidellites and montmorillonites.

The bridged clays can be produced by a process comprising the following steps:
  (a) treating an aqueous suspension of a natural or synthetic clay with an aqueous solution containing at least one hydroxide of at least one metal,
  (b) eliminating excess metal hydroxide which has not reacted on the clay and drying of the treated clay, and
  (c) heat-treating tale treated clay, thus producing the bridged clay.

To prepare the bridged clays in accordance with the invention, it is also possible to carry out only steps (a) and (b).

Bridging of the clays may be effected by means of hydroxides of the metals indicated above.

Preferably, the catalyst used in the process of the invention is a beidellite or a montmorillonite which is bridged by means of aluminum hydroxide, for example using the process described in FR-A-2,563,446.

Other exemplary catalysts which are also suitable for the present invention include the natural zeolites such as, for example, chabazite, clinoptilolite, erionite, mordenite, phillipsite and offretite.

Synthetic zeolites are well suited for carrying out the process of this invention, such as zeolite ZSM-5, zeolite Y, ferrierite, zeolite X of type faujasite, zeolite of type L, mordenite and zeolite ZSM-11, mazzite and offretite. Irrespective of the zeolite, it is treated to render same acid.

Synthetic zeolites are the preferred and more particularly commercial zeolites which are in the following forms:
  (i) zeolites in acid form such as zeolites ZSM-5 or aluminum silicalite having an Si/Al molar ration of 10 to 500; zeolites Y, in particular zeolites obtained after dealumination (for example by hydrotreatment, washing by means of hydrochloric acid, or treatment with SiCl$_4$), and more particularly of zeolites US-Y having an Si/Al molar ration of higher than 3 and preferably ranging from 6 to 60; and zeolites such s ferrierite having an Si/Al molar ration of from 5 to 10;
  (ii) zeolites in exchangeable sodium or potassium form, such as zeolite X of faujasite type having an Si/Al molar ratio of from 1 to 1.5, zeolite of type L having an Si/Al molar ratio of from 3 to 3.5, mordenite having an Si/Al molar ratio of from 5 to 6 and zeolite ZSM-11 having an Si/Al molar ratio of from 5 to 30, and
  (iii) zeolites both in acid form or in exchangeable sodium or potassium form such as mazzite having an Si/Al molar ratio of 3.4 and offretite having an Si/Al molar ratio of 4.

In accordance with the process of the invention, the zeolite used is an acidified zeolite.

To acidify the zeolite, if necessary, conventional treatments are employed. Thus, it is possible to exchange the alkaline cations by subjecting the zeolite to a treatment which is carried out using ammonia, thus resulting in an exchange of the cation by an ammonium ion and then calcining the exchanged zeolite in order to thermally decompose the ammonium cation and replace it by an ion H$^+$.

The amount of ammonia to be used is at least equal to the amount required to exchange all of the alkaline cations to provide ions HN$_4^+$.

Therefore, at least from $5 \cdot 10^{-3}$ to $10^{-5}$ mole of ammonia per gram of zeolite is used.

The exchange reaction in respect of the cation which is exchangeable by NH$_4^+$ is conducted at a temperature which ranges from ambient temperature to the reflux temperature of the reaction medium. The operation is carried out for several hours and may be repeated.

The zeolites may also be acidified by subjecting them to a conventional acid treatment. That treatment may be carried out via addition of an acid such as, in particular, hydrochloric acid, sulfuric acid, nitric acid, perchloric acid, phosphoric acid and trifluoromethanesulfonic acid.

In a preferred technique, the zeolite is acidified using a volume of acid having a normality of from 0.1 to 2N per gram of zeolite, ranging from 10 ml/g to 100 ml/g. This treatment may be carried out in a single step or, preferably, in a plurality of successive steps.

It is also within the scope of the present invention to use a modified acid zeolite, for example zeolites of type ZSM-5 and ZSM-11, in which a fraction of the aluminum is replaced by an element such as iron, gallium, boron, indium, chromium, scandium, cobalt, nickel, beryllium, zinc, copper, antimony, arsenic, vanadium, or a mixture thereof.

Other solid catalyst having acid properties which are suitable for carrying out the process of the invention include, for example, the phosphates, such as, in particular, the phosphates of boron, aluminum or gallium.

Advantageously, lamellar or foliated phosphates of tetravalent metals can be used, corresponding to the formula $\alpha$-M(HPO$_4$)·pH$_2$O, in which M is a tetravalent metal selected from among titanium, germanium, zirconium and tin and p is a number of less than 2. Such compounds are described in the literature, for example, in Albertie et al, *J. Inorg. Nucl. Chem.*, 40, pages 1,113 (1978).

Lamellar phosphonates of tetravalent metals can also be used, more particularly lamellar phosphonates of zirconium (U.S. Pat. No. 4,435,899).

Oxides which are acidified are also suitable par this invention. Sulfated, chlorinated or fluorinated oxides are exemplary thereof. Preferred are the sulfated oxides of titanium, zirconium or iron. Such oxides are described, inter alia, in EP-A-0,397,553.

It is also possible to use a catalyst of Lewis acid type.

By the term "Lewis acid" is intended the normal definition, connoting compounds which accept pairs of electrons.

In particular, the Lewis acids can be used referred to in the text edited by G. A. Olah, *Friedel-Crafts And Related Reactions*, volume I, pages 191 to 197 (1963).

The Lewis acids which can be used in the subject process are more particularly the halides of elements of Groups 3a, 4a, 5a, 1b, 2b,3b, 4b, 5b, 6b, 7b and 8 of the Periodic Table, such as chlorides, bromides, fluorides and iodides of aluminum, tin, phosphorous, antimony, arsenic, bismuth, titanium tantalum, tellurium, selenium, zirconium, vanadium, samarium, niobium, tungsten, platinum, molybdenum, iron, cobalt, nickel, zinc and cadmium.

Specific examples of such halides include aluminum chloride, titanium tetrachloride, zirconium tetrachloride, vanadium trichloride, samarium chloride, antimony pentafluoride, bismuth trichloride and stannous chloride.

In a preferred embodiment of the invention, hydrofluoric acid, perchloric acid, trifluoromethanesulfonic acid, methanesulfonic acid and sulfonic resins of NAFION type comprise the acid catalyst.

As regards the sulfur-containing compound which is optionally present in the process of the invention, the following are more particularly preferred:

(a) sulfur-containing inorganic compounds:
  (i) sulfur halides, preferably sulfur monochloride or sulfur dichloride,
  (ii) thiosulfates of ammonium, alkali metals or alkaline earth metals, preferably ammonium, sodium or potassium thiosulfate,
  (iii) hydrogen sulfide or precursors thereof, such as, for example, calcium or potassium sulfide which, when added to the acidic reaction medium, form hydrogen sulfide;

(b) sulfur-containing organic compounds:
  (i) mercaptans, in particular alkylmercaptans, phenylmercaptans and phenylalkylmercaptans, such as, for example, ethylmercaptan, butylmercaptan, 1-nonylmercaptan and benzylmercaptan,
  (ii) thioalohols, such as, for example, 2-mercaptoethanol and 3-mercapto-2-butanol,
  (iii) thiophenols, such as, in particular, thiophenol, o-thiocresol, m-thiocresol, p-thiocresol, thioxylenol, p-methylthiophenol, o-ethylthiophenol, thiohydroquinone and thionaphthol,
  (iv) thioorganic acids, their salts or esters thereof, such as thioacetic acid, thiopropionic acid, thiolactic acid, thiosalicyclic acid, 2-mercaptoethanesulfonic acid, 3-mercaptopropanesulfonic acid, mercaptosuccinic acid, thioglycolic acid, and methyl and ethyl thioglycol,
  (v) cation exchange resins modified by reaction with an alkyl mercaptoamine, preferably resins comprising a polystyrene skeleton bearing sulfonic groups as described above, having reacted with an alkyl mercaptoamine, preferably that with a primary amine group and still more preferably that having from 1 to 4 carbon atoms and, in particular, 2-mercaptoethylamine, 2-mercaptoisopropylamine and 3-mercaptobutylamine.

The preferred sulfur-containing compounds are alkylmercaptans and benzylmercaptan.

In accordance with the process of the invention, the preparation of a p-fuchsone is carried out by reacting the phenolic compound of formula (I) with the ketonic compound of formula (II) in the presence of the acid catalyst and, optionally, an ionizable sulfur-containing compound.

The amount of phenolic compound of formula (I) used, expressed with respect to the ketonic compound of formula (II), is generally at least equal to the stoichiometric amount. A molar ratio between the phenolic compound of formula (I) and the ketonic compound of formula (II) is advantageously selected at from 1 to 20, preferably from 1 to 10.

With respect to the acid catalyst, the amount of acid, expressed by the ratio of equivalents of protons to the number of moles of ketonic compound of formula (II), advantageously ranges from $1 \cdot 10^{-3}$ to 1.0, preferably from $5 \cdot 10^{-3}$ to 0.5.

It is also possible to use the acid as the reaction medium, in particular in the case of hydrofluoric acid and trifluoromethanesulfonic acid. Thus, the aforesaid ratio may be higher than 1.0 and it may even be very high, exceeding 20. Preferably, it ranges from 5.0 to 10.

If the catalyst is a solid heterogeneous catalyst, the amount to be used is determined such that the catalyst constitutes from 0.1% to 20% and preferably from 0.5% to 10% by weight with respect to the phenolic compound of formula (I). However, if the process is carried out continuously, for example by reacting a mixture of phenolic compound of formula (I) and ketonic compound of formula (II) over a fixed catalyst bed, the catalyst/ketonic compound of formula (II) ratios are not significant and at a given moment it will be possible to have an excess by weight of catalyst with respect to the ketonic compound of formula (II).

The amount of sulfur-containing cocatalyst compound used, expressed with respect to the ketonic compound of formula (II), is advantageously selected such that the molar ratio between the sulfur-containing compound and the ketonic compound of formula (II) ranges from 0.001 to 1.0, preferably from 0.005 to 0.20.

Preparation of the fuchsone according to the process of the invention is advantageously carried out at a temperature which may range from 45° C. to 200° C.

In a preferred embodiment of the invention, the reaction temperature ranges from 60° C. to 150° C.

The reaction is advantageously carried out under atmospheric pressure.

Preparation of the fuchsone according to the invention may also be carried out in the presence of an organic solvent.

One of the advantages of using an organic solvent is the option of eliminating water from the reaction medium by azeotropic distillation.

It is possible to use any organic solvent which is inert under the conditions of reaction. Exemplary such organic solvents well suited for the present invention include:

(i) aliphatic and/or aromatic hydrocarbons and, more particularly, paraffins such as, preferably, hexane, heptane, octane, nonane, decane, undecane, dodecane or tetradecane, cyclohexane, methylcyclohexane; and aromatic hydrocarbons such as, more especially, xylenes, cumene, and petroleum cuts comprising a mixture of alkylbenzenes, in particular cuts of Solvesso® type, and (ii) aliphatic or aromatic halogenated hydrocarbons, for example, perchlorinated hydrocarbons such as, in particular, carbon tetrachloride, tetrachloroethylene, hexachloroethane and hexachloropropene, partially chlorinated hydrocarbons such as methylene chloride, dichloroethane, tetrachloroethane, trichlorethylene, 1-chlorobutane, 1,2-dichlorobutane, monochlorobenzene, 1,2-dichlorobenzene, 1,3-dichlorobenzene, 1,4-dichlorobenzene, or mixtures of different chlorobenzenes; monobromobenzene or mixtures of monobromobenzene with one or more dibromobenzenes.

A mixture of organic solvents can also be used.

The concentration of reactants in the organic solvent may vary widely. The concentration of non-enolizable ketone in the organic solvent may vary, for example, from 0.1 to 2 mole/liter, preferably from 0.2 to 1.0 mole/liter.

From a practical standpoint, the process according to the invention is simple to carry out, whether continuously or discontinuously.

The different reactants may be introduced in any order. Preferably, the order for the introduction of the reactants is as follows: first introduced is the phenolic compound of formula (I), next the ketonic compound of formula (II) and the acid catalyst and, optionally, the ionizable sulfur-containing compound. It is also possible to add an organic solvent.

The reaction medium is heated to the desired temperature, while maintaining the reaction medium in an agitated condition.

Over the course of the reaction, water is formed in the reaction medium. One preferred embodiment of the invention entails limiting the concentration of water in the reaction medium by removing it as it is formed, by any known means, in particular by azeotropic distillation.

At the end of the reaction, the fuchsone formed is recovered from the reaction medium.

The procedure begins by separating the catalyst. If the catalyst is a homogenous catalyst, the reaction mass is washed with water and a suitable organic solvent is added to extract the unreacted reactants and the fuchsone formed. Exemplary such organic solvents include, more particularly, ethyl acetate and dichloromethane. The acid catalyst is transferred into the aqueous phase and the fuchsone formed and possibly the reactant which have not been converted are recovered in the organic phase.

In the event of a hererogenous acid catalyst, the solid acid catalyst is washed with water in the presence of an organic solvent which extracts the unreacted reactants and the fuchsone formed. The catalyst is separated using the conventional solid/liquid separation techniques, preferably via filtration, and then the organic phase is separated.

It is possible to recover the fuchsone from the organic phase by preparative liquid chromatography over a silica column.

It is also possible to separate the fuchsone from the unconverted phenolic compound and the ketonic compound of formula (II) by the usual means, more especially by crystallization.

With respect to the sulfur-containing compound, depending on its nature, it may be present either in the aqueous phase or in the organic phase. It can be recovered via the usual separation processes, in particular by distillation.

The process according to the present invention presents numerous advantages. For example, readily available raw materials can be used and the fuchsone is prepared at a very good level of selectivity.

The embodiment of including an ionizable sulfur-containing compound permits increasing the reaction speed for formation of the fuchsone, no an appreciable degree.

Thus, fuchsones are prepared, for example having the following general formula (III):

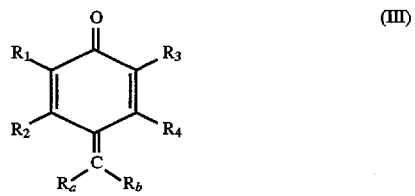

(III)

in which formula (III) the different symbols $R_1$, $R_2$, $R_3$, $R_4$, $R_a$ and $R_b$ are as defined above, namely, $R_a$ and $R_b$, which may be identical or different, are each a hydrocarbon radical having from 3 to 30 carbon atoms, with the carbon atoms of each radical $R_a$ and $R_b$ in the α-position with respect to the carbon atom from which they depend being tertiary carbons, and $R_1$, $R_2$, $R_3$ and $R_4$, which may be identical or different, are each a hydrogen atom or any inert substituent, with the proviso that $R_1$ and $R_2$ and/or $R_3$ and $R_4$ borne by two adjacent carbon atoms may together form, with the carbon atoms from which they depend, a ring member, preferably an unsaturated or aromatic carbocycle having from 4 to 7 carbon atoms.

The subject process and particularly suited for the preparation of diphenylfuchsone from phenol and benzophenone.

The process of the invention permits preparation of a fuchsone of formula (III), but it will be appreciated that a fraction of the fuchsone formed may be in a hydrated state, referred to as a carbinol, and which can be represented by the following formula (IV):

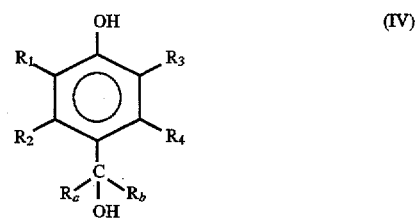

(IV)

in which formula (IV) the various symbols $R_1$, $R_2$, $R_3$, $R_4$, $R_a$ and $R_b$ are as defined above.

The fuchsone/carbinol molar ratio varies with the amount of water used in the treatment of the reaction mass and with the pH of the medium. For example, such ratio can range from 1 to 2.

The present invention also features a process for the preparation of a para-dihydroxylated aromatic compound, comprising reacting an oxidizing agent with a p-fuchsone.

The starting material is a p-fuchsone in anhydrous or hydrated state, or a mixture of the two. A p-fuchsone corresponding to the above general formula (III) and/or (IV) is preferred.

Among the compounds of formula (III) and/or (IV), more preferred are those in which $R_1$, $R_2$, $R_3$ and $R_4$, which may be identical or different, represent $R_O$, defined above in respect of the formula (I), or at least one of $R_1$, $R_2$, $R_3$ and $R_4$, which may be identical or different, is a radical $R_7$, also as defined above in respect of formula (I).

Exemplary radicals $R_a$ and $R_b$ are the branched alkyl radicals having at least three carbon atoms and aryl radicals having at least 6 carbon atoms and, more particularly, tert-butyl, tert-pentyl, tert-hexyl or phenyl radicals, or optionally substituted such radicals.

The fuchsones of formula (III) and (IV) may bear one or more substituents $R_1$, $R_2$, $R_3$ or $R_4$. Exemplary such substituents are presented above. Any substituent may be present on the ring as long as it does not interfere with the actual preparation of the desired final product.

The fuchsones which are well suited for oxidation according to the present invention may be represented more particularly by the following general formulae (IIIa) and/or (IVa):

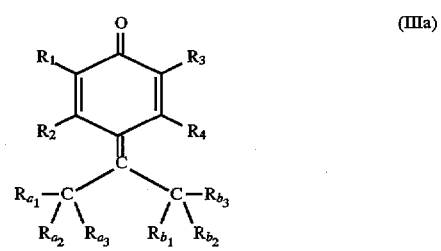

(IIIa)

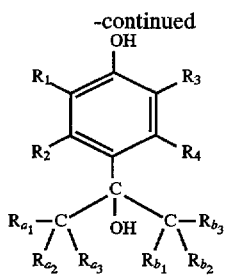

in which formulae (IIIa) and (IVa) $R_{a1}$, $R_{a2}$ and $R_{a3}$ and $R_{b1}$, $R_{b2}$ and $R_{b3}$, which may be identical or different are each a branched or straight chain alkyl radical having from 1 to 10 carbon atoms, a cyclohexyl, phenyl or naphthyl radical, or an optionally substituted such radical, with the proviso that $R_{a1}$, $R_{a2}$ and $R_{a3}$ on the one hand, and $R_{b1}$, $R_{b2}$ and $R_{b3}$ on the other, may together form, with the carbon atom from which they depend, an optionally substituted benzene or naphthalene ring; or $R_1$, $R_2$, $R_3$ or $R_4$, which may be identical or different, are each a hydrogen atom, a branched or straight chain alkyl radical having from 1 to 4 carbon atoms, a branched or straight chain alkoxy radical having from 1 to 4 carbon atoms, a hydroxyl group, a halogen atom, a group —$CF_3$, a cyclohexyl radical, or a phenyl radical, with the proviso that $R_1$ and $R_2$ and/or $R_3$ and $R_4$ which are borne by adjacent carbon atoms may together form, with the carbon atoms form which depend, a benzene ring.

By the expression "optionally substituted" is intended that one or more substituents is or are present on the cyclic radicals. Exemplary such substituents, symbolized by Y, are set forth hereinbelow.

Still more preferably, the compounds selected are of formula (IIIa) and/or (IVa) in which one of the radicals $R_1$, $R_2$, $R_3$ and $R_4$ is a hydroxyl group, a methyl radical or a methoxy radical and the other three are hydrogen atoms.

Among the fuchsones which correspond to the formulae (IIIa) and/or (IVa), particularly preferred are the fuchsones which correspond to the following formulae (IIIb) and/or (IVb):

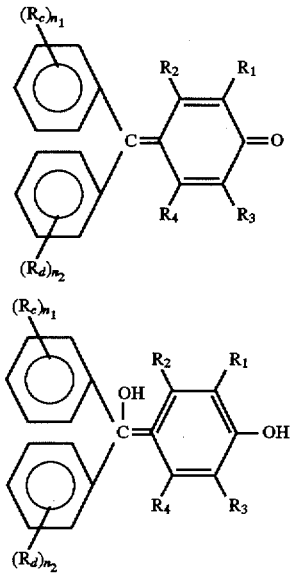

in which $R_1$, $R_2$, $R_3$ and $R_4$, which may be identical or different, are each a hydrogen atom, a branched or straight chain alkyl radical having from 1 to 4 carbon atoms, a branched or straight chain alkoxy radical having from 1 to 4 carbon atoms, a hydroxyl group, a halogen atom, a group —$CF_3$, a cyclohexyl radical, or a phenyl radical, with the proviso that $R_1$ and $R_2$ and/or $R_3$ and $R_4$ which are borne by two adjacent carbon atoms may together form, with the carbon atoms from which they depend, a benzene ring; $R_c$ and $R_d$, which may be identical or different, are each a hydrogen atom or an inert substituent; and $n_1$ and $n_2$, which may be identical or different, are each a number equal to 0, 1, 2 or 3.

The substituent Y is selected such that it does not react under the acid conditions of the invention.

Exemplary such substituents include branched or straight chain alkyl radicals having from 1 to 4 carbon atoms, the phenyl radical, the alkoxy $R_{10}$—O radicals in which $R_{10}$ is a branched or straight chain alkyl radical having from 1 to 4 carbon atoms or a phenyl radical, the hydroxyl group, and halogen atoms, preferably chlorine, bromine or fluorine atoms.

Preferred fuchsones are those corresponding to the general formulae (IIIb) and/or (IVb) in which $R_c$ and $R_d$, which may be identical or different, are each a hydrogen atom or a substituent as described above; $R_c$ and $R_d$ are preferably in the position 4,4' and $n_1$ and $n_2$, which may be identical or different, are each equal to 0 or 1.

The preferred fuchsones which correspond to formulae (IIIb) and/or (IVb) are those in which $R_c$ and $R_d$, which may be identical or different, are each a hydrogen atom, a methyl, ethyl, tert-butyl or phenyl radical, a methoxy or ethoxy radical, or a hydroxyl group, with $R_c$ and $R_d$ preferably being in position 3,3' or position 4,4'.

Specific examples of fuchsones which are well suited for reaction with an oxidizing agent according to the invention include the following fuchsones and/or carbinols thereof:

(a) diphenylfuchsone and/or its carbinol:

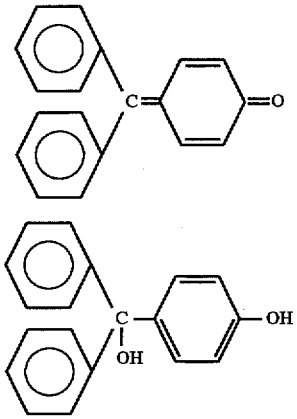

(b) rosolic acid and/or its carbinol:

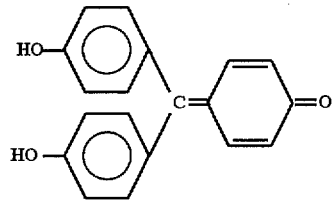

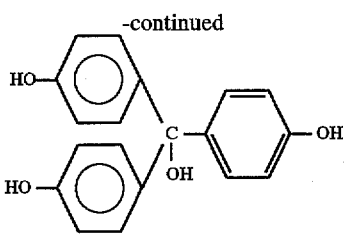

(c) diphenylmethylfuchsone and/or its carbinol:

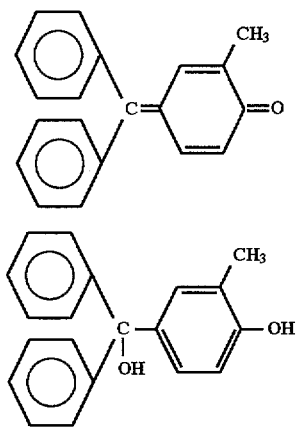

Any fuchsone, irrespective of the manner of the preparation thereof, can be used in the oxidation process of the invention. Thus, fuchsones can be used which are prepared via the processes described, in particular, by I. S. Ioffe et al, *J. Gen. Chem. USSR*, 19, pages 917–28 (1949) and H. Burton et al, *J. Chem. Soc.*, 3089–3090 (1955).

Exemplary oxidizing agents which are well suited for this embodiment of the process of invention include hydrogen peroxide, peracids such as peracetic acid, hydroperoxides such as tertiobutyl hydroperoxide, cyclohexyl hydroperoxide and cumyl hydroperoxide.

Among these oxidizing agents, hydrogen peroxide is the preferred.

The hydrogen peroxide used according invention may be in the form of an aqueous solution or an organic solution.

The aqueous solutions, being commercially more readily available, are the preferred.

The concentration of the aqueous solution of hydrogen peroxide, although not critical, per se, is selected such as to introduce the least possible amount of wader into the reaction medium. Generally, an aqueous solution of hydrogen peroxide is used, with at least 20% by weight of $H_2O_2$ and preferably about 70% thereof.

The amount of hydrogen peroxide is preferably equal to the stoichiometric amount, namely, 1 mole of $H_2O_2$ for 1 mole of fuchsone of formula (III) and/or (IV). It is possible to use a slight excess, up to 20% of the stoichiometric amount.

In a preferred embodiment of the invention, the fuchsone is reacted with the oxidizing agent in the presence of an acid catalyst.

An acid catalyst which is preferred is a strong acid. The term "strong acid" is intended an acid having a pKa in wader of less than −0.1 and preferably less than −0.1.

The pKa is the ionic dissociation constant of the acid/base pair, when water is used as the solvent.

Among the acids which correspond to this definition, it is preferable to use those which are stable in relation to oxidation by means of hydrogen peroxide.

Particularly exemplary thereof are the oxyacids which either may or may not be halogenated, such as sulfuric acid, pyrosulfuric acid, perchloric acid, halosulfonic acids such as fluorosulfonic acid, chlorosulfonic acid or trifluoromethane sulfonic acid, methanesulfonic acid, ethanesulfonic acid, ethanedisulfonic acid, benzenesulfonic acid, benzenedisulfonic acids, toluenesulfonic acids, naphthalenesulfonic acids and naphthalenedisulfonic acids.

Among such acids, perchloric acid, trifluorethanesulfonic acid, paratoluenesulfonic acid, chlorosulfonic acid, fluorosulfonic acid and methanesulfunic acid are the preferred.

More preferred are perchloric acid and trifluoromethanesulfonic acid.

The amount of acid, expressed by the ratio of the number of equivalents of protons to the number of moles of hydrogen peroxide, advantageously ranges from about $1 \cdot 10^{-4}$ to 1.0.

A preferred embodiment of the process of the invention entails selecting a $H^+/H_2O_2$ ratio of from $1 \cdot 10^{-3}$ to 0.1.

The reaction is advantageously carried out in the liquid phase. Thus, the procedure is initiated by solubilizing the fuchsone in an organic solvent which may be the phenolic compound of formula (I) as described hereinafter, or any protic or aprotic, polar or apolar organic solvent, insofar as it is suitable according to the present invention.

A number of requirements govern the selection of the solvent.

The organic solvent is to be stable under the conditions of the invention. Solvents which are not stable in the reaction medium and which undergo degradation due to oxidation are not suitable per the present invention.

The organic solvent preferably solubilizes both the oxidizing agent and the fuchsone present.

In addition, it is desirable for the organic solvent not be too basic, namely, its basicity should be such that it has a "donor number" of lower than 25. To assess the basicity of a solvent, reference is made to its "donor number". It will be appreciated that the "donor number" which is referred to by the abbreviation DN provides an indication of the nucleophilic character of the solvent and indicates its suitability to form its duplet.

The text by Christian Reinhardt, *Solvents and Solvent Effects In Organic Chemistry*, VCH page 19 (1988), indicates the definition of the "donor number" which is defined as the negative $(-\Delta H)$ of the enthalpy (Kcal/mole) of the interaction between the solvent and antimony pentachloride in a dilute solution of dichloroethane.

Exemplary organic solvents useful in the oxidation process of the invention, include, in particular:

(i) aliphatic or aromatic nitriles, such as acetonitrile, propionitrile, butanenitrile, isobutanenitrile, benzonitrile and benzyl cyanide, (ii) aliphatic, cycloaliphatic or aromatic ethers, and more particularly diethyl oxide, dipropyl oxide, diisopropyl oxide, dibutyl oxide, methyltertiobutylether, dipentyl oxide, diisopentyl oxide, ethylene glycol dimethylether (or 1,2-dimethoxyethane), diethyleneglycol dimethylether (or 1,5-dimethoxy-3-oxapentane), dioxane and tetrahydrofuran, (iii) chlorinated aliphatic hydrocarbons, for example, dichloromethane, tetrachloroethane and dichloromethane, and (iv) alcohols such as methanol, ethanol, isopropanol and tertiobutanol.

A mixture of solvents can also be used and, in particular, a mixture of phenolic compound of formula (I) and an organic solvent.

The amount of organic solvent used depends on the solubility of the fuchsone in the organic solvent.

The concentration of fuchsone in the organic solvent may vary widely. It advantageously ranges from 0.1 to 2 moles/liter.

According to this embodiment of the process of the invention, the fuchsone and the oxidizing agent are reacted, optionally in the presence of an acid catalyst, at a temperature which may range from 20° C. to 150° C.

In a preferred embodiment of this variant of the process of the invention, such temperature ranges from 30° C. to 80° C.

The reaction is advantageously carried out under atmospheric pressure.

From a practical standpoint, the oxidation process according to the invention is simple to carry out, whether continuously or discontinuously.

The different reactants may be introduced in any order insofar as the oxidizing agent is introduced last. Preferably, the following order is selected for the reactants: the fuchsone of formula (III) and/or (IV), the reaction solvent and the acid catalyst.

The reaction medium is heated to the desired temperature and then the oxidizing agent, preferably a solution of hydrogen peroxide, is progressively added.

At the end of the reaction, the hydroxylation products are separated via conventional technique, in particular by distillation.

A preferred embodiment of the oxidation process of the invention entails providing a fuchsone of formula (III) and/or (IV) prepared as described above, by reacting a phenolic compound having a hydrogen atom in the para-position to the hydroxyl group with a non-enolizable ketonic compound, in the presence of a catalytically effective amount of an acid.

Per the oxidation process of the invention, preparation of a p-dihydroxylated aromatic compound is carried out by reacting the isolated fuchsone with the oxidizing agent. The fuchsone is isolated in accordance with any method of separation, an example of which is indicated above.

In another embodiment of the invention, the synthesis of the fuchsone is combined with reaction thereof with the oxidizing agent.

For that purpose, the oxidizing agent is introduced directly into the reaction medium comprising the fuchsone.

The oxidizing agent is of the same nature as described above.

The reaction conditions set forth hereinbefore (temperature, proportions, etc.) still apply.

It may be that an acid catalyst need not be added again at the stage of reaction of the fuchsone with the oxidizing agent, insofar as the amount of acid used for preparing the fuchsone is adequate.

At the end of the reaction, the hydroxylation products are separated by the usual means, in particular by distillation.

The process of the invention makes it possible to selectively prepare para-dihydroxylated aromatic compounds.

Another advantage of the process of the invention is that reaction of the fuchsone of formula (III) and/or (IV) with the oxidizing agent produces a para-dihydroxylated aromatic compound and a ketone of formula (II); that ketone can be recycled to the operation of synthesizing the fuchsone of formula (III) and/or (IV).

It has also been found that a p-dihydroxylated aromatic compound can be prepared by oxidation of a phenolic compound, the p-fuchsone then serving as a reaction catalyst.

Thus, the present invention also features a process for the preparation of a p-dihydroxylated aromatic compound by reacting phenolic compound having a hydrogen atom in the para-position with hydrogen peroxide in the presence of a catalytically effective amount of a strong acid, and wherein the reaction is carried out in the presence of a catalytically effective amount of a p-fuchsone.

This embodiment of the present invention is more particularly applicable to the phenolic compound of general formula (I) as hereinbefore described.

Among the phenolic compounds of formula (I) which can be used in this embodiment of the invention, phenol, anisole, orthocresol and metacresol are particularly representative.

As indicated above, the principal characteristic of the embodiment of the invention is the use of a p-fuchsone as a catalyst.

The fuchsones used preferably correspond to formulae (III) and/or (IV) as described above, more particularly formulae (IIIa) and/or (IVa), and still more preferably formulae (IIIb) and/or (IVb).

The fuchsones which are the preferred are dipheylfuchsone, rosolic acid and diphenylmethylfuchsone.

It is possible to use any fuchsone and, in particular, those which are described by I. S. Ioffe et al, *J. Ge. Chem. USSR*, 19, pages 917–28 (1949) and H. Durton et al, *J. Chem. Soc.*, 3089–3090 (1955), but it is preferred to use those prepared in accordance with the process of the invention by reacting a phenolic compound with a non-enolizable ketone.

As regards the selection of catalyst, the nature of the p-fuchsone should be determined in such mater that it liberates a p-dihydroxylated aromatic compound identical to that which is to be prepared by subsequent oxidation of the beginning phenolic compound.

According to this embodiment of the invention, the presence of p-fuchsone over the course of the oxidation of the phenolic compound of formula (I) influences the regioselectivity of the reaction.

The compound is used in a catalytic amount.

In general, the amount of fuchsone of formula (III) and/or (IV) is less than 1.0 mole per mole of hydrogen peroxide. It typically ranges from $1 \cdot 10^{-3}$ mole to 1.0 mole, preferably from 0.05 to 0.5.

The solutions of hydrogen peroxide as described above are used.

The amount of hydrogen peroxide mat be up to 1 mole of $H_2O_2$ per 1 mole of phenolic compound of formula (I).

However, to attain an industrially acceptable yield, it is preferable to use a hydrogen peroxide/phenolic compound of formula (I) molar ratio of from 0.01 to 0.3 and preferably from 0.05 to 0.10.

In order to have a sufficient reaction speed, the initial water content of the medium is limited to 20% by weight and preferably to 10% by weight.

The contents by weight specified are expressed with respect to the mixture of the phenolic compound of formula (I)/hydrogen peroxide/water.

That initial water corresponds to the water introduced with the reactants and, in particular, with the hydrogen peroxide.

This embodiment of the invention entails the use of a strong acid. Exemplary strong acids are those used for oxidation of the p-fuchsone.

More particularly, perchloric acid, trifluoromethanesulfonic acid or methanesulfonic acid are used.

The amount of acid, expressed by the ratio of the number of equivalents of protons to the number of moles of hydrogen peroxide, advantageously ranges from about $1 \cdot 10^{-4}$ to about 1.0.

In this embodiment of the invention, an $H^+/H_2O_2$ ratio of from $1·10^{-3}$ to 0.1 is preferably employed.

Also in this embodiment, an aprotic polar organic solvent is used having certain characteristics in terms of polarity and basicity. The presence of such solvent can improve the regioselectivity of reaction.

A first variant of this embodiment of the invention entails using a polar, weakly basic organic solvent, namely, a solvent having a polarity such its dielectric constant is higher than or equal to 20 and a basicity such that is has "donor number" of less than 25.

A second variant of this embodiment of the invention entails using a weakly polar but basic organic solvent, namely, a solvent having a polarity such that its dielectric constant is less than about 20 and a basicity such that is has a "donor number" of greater than or equal to 15 and less than 25.

A number of requirements govern the selection of the organic solvent.

A first characteristic of the organic solvent is that it is to be aprotic and stable in the reaction medium.

By the term "aprotic solvent' is intended a solvent which, according to Lewis theory, does not have any protons to liberate.

Solvents which are not stable in the reaction medium and which experience degradation either by oxidation or by hydrolysis are excluded from the present invention. Exemplary such reaction solvents which are not suitable for the invention include the solvents of the ester type derived from carboxylic acids, such as, in particular, methyl or ethylacetate, methyl or ethylphthalate, methylbenzoate, etc.

The organic solvents which are indeed suitable for this embodiment of the invention must comply with certain requirements in terms of their polarity and their basicity, which is characterized by the donor number.

A first class of organic solvents which is completely suitable comprises the polar and weakly basic organic solvents.

In accordance with this embodiment of the invention, an organic solvent which has a dielectric constant of greater than or equal to 20 is selected. The upper limit is not critical. It is preferably to use an organic solvent having a high dielectric constant, preferably ranging from 25 to 75.

The organic solvent having the aforesaid polarity characteristics must also satisfy certain conditions in regard to basicity. Indeed, the solvent is not to be excessively basic. To determine if a solvent satisfies this requirement, it basicity is assessed by referring to the "donor number." A polar organic solvent having a donor number of less than 25 and preferably less than or equal to 20 is selected. The lower limit is not critical. An organic solvent having a donor number of from 2 to 17 is preferably selected.

As regards other classes of solvents, the characteristics of said solvents are indicated below.

The solvents belonging to this category are weakly polar, but basic organic solvents.

According to this embodiment of the invention, an organic solvent which has a dielectric constant of less than about 20 is selected. The lower limit is not critical. It is preferable to use an organic solvent having a low dielectric constant, preferably ranging from 2 to 15.

With respect to its basicity, it is to be such that it has a "donor number" greater than or equal to 15 and less than 25. An organic solvent having a donor number of from 15 to 25 is preferably employed.

In order to ascertain of the organic solvent complies with the conditions indicated above in terms of dielectric constant, compare, inter alia, the tables set forth in *Techniques of Chemistry. II, "Organic solvents"*, pages 536 et seq, 3rd edition (1970).

As regards the requirements concerning basicity of the organic solvent to be used, see again the definition of the "donor number" indicated above.

Exemplary polar aprotic organic solvents complying with the aforesaid basicity characteristics, particularly representative are the following:

(i) nitro compounds, such as nitromethane, nitroethane, 1-nitropropane, 2-nitropropane or mixtures thereof, and nitrobenzene, (ii) aliphatic or aromatic nitriles, such as acetonitrile, propionitrile, butanenitrile, isobutanenitrile, benzonitrile and benzyl cyanide, (iii) tetramethylene sulfone (sulfolane), and (iv) propylene carbonate.

A mixture of such solvents can also be used.

Among the above solvents, acetonitrile is the preferred.

With respect to still other suitable solvents, the following weakly polar, basic aprotic solvents can be used:

(i) aliphatic, cycloaliphatic or aromatic ethers and, more particularly, diethyl oxide, dipropyl oxide, diisopropyl oxide, dibutyl oxide, methyltertibutylether, dipentyl oxide, diisopentyl oxide, ethyleneglycol dimethylether (or 1,2-dimethoxyethane), diethyleneglycol dimethylether (or 1,5-dimethoxy-3-oxapentane), dioxane and tetrahydrofuran, (ii) neutral phosphoric esters, such as, in particular, trimethyl phosphate, triethyl phosphate, butyl phosphate, triisobutyl phosphate and tripentyl phosphate, and (iii) ethylene carbonate.

A mixture of such solvents can also be used.

The amount of organic solvent used is determined in dependence on the nature of the organic solvent selected.

Thus, when using a polar but weakly basic organic solvent, it is determined in such manner that the molar ratio between the number of moles of organic solvent and the number of moles of phenolic compound of formula (I) ranges from 0.1 to 2.0, preferably from 0.25 to 1.0.

If a weakly polar and basic organic solvent is used, the amount employed is determined such that the molar ratio between the number of moles of organic solvent and the number of moles of phenolic compound of formula (I) ranges from 0.01 to 0.25, preferably from 0.025 to 0.15.

The hydrogen peroxide and the fuchsone corresponding to formula (III) and/or (IV) are employed under the reaction conditions described above.

In accordance with this embodiment of the invention, hydroxylation of the phenolic compound of formula (I) is carried out at a temperature ranging from 45° C. to 150° C.

Preferably, a temperature at from 60° C. to 110° C. is selected.

This reaction is advantageously carried out under atmospheric pressure.

From a practical standpoint, this embodiment of the invention is simple to carry out, either continuously or discontinuously.

The different reactants can be introduced in any order. Preferably the order in which the reactants are introduced is as follows: phenolic compound of formula (I), fuchsone of formula (III) and/or (Iv) and the acid catalyst.

The reaction medium is heated to the desired temperature then the hydrogen peroxide solution is progressively added.

At the end of the reaction, the phenolic compound which has not ben converted and the ketone formed are separated from the hydroxylation products by conventional technique, in particular by distillation.

The process of the invention thus permits obtaining a mixture of dihydroxylated aromatic compounds, namely, the ortho and para isomers, with a very good level of selectivity in respect of the para isomer, since the para/ortho ratio is markedly higher than 1 and preferably ranges from 1.5 to 10.0.

In order to further illustrate the present invention and the advantages thereof, the following specific examples are given, it being understood that same are intended only as illustrative and in nowise limitative.

EXAMPLES 1 TO 51

Examples 1 to 24 relate to the preparation of p-fuchsone.

Examples 25 to 51 illustrate an alternative embodiment of the process according to the invention, employing an ionizable sulfur-containing compound.

In said Examples, the following abbreviations have the following definitions:

$$TT_{KETONE} = \frac{\text{number of moles of ketone converted}}{\text{number of moles of ketone introduced}} \%$$

$$RR_{FUCHSONE} = \frac{\text{number of moles of fuchsone formed}}{\text{number of moles of ketone introduced}} \%$$

$$RT_{FUCHSONE} = \frac{\text{number of moles of fuchsone formed}}{\text{number of moles of ketone converted}} \%$$

With respect to the indicated results obtained, the RR and RT are reported without distinguishing fuchsone from its hydrated form, carbinol. The term fuchsone therefore connotes the mixture of fuchsone and its carbinol. As indicated above, the amount of fuchsone hydrated depends on the reaction conditions: that ratio is generally close to 1.5.

EXAMPLE 1

The following reagents were introduced into a 100 ml glass round-bottom flask provided with a central agitation system, a condenser, a dropping funnel and a thermometer:
(i) 19.8 g (0.2 mole) of phenol,
(ii) 18.2 g (0.1 mole) of benzophenone, and
(iii) 7.5 g (0.05 mole) of trifluoromethanesulfonic acid, $CF_3SO_3H$.

The reaction mixture was heated to the selected reaction temperature of 70° C., while maintaining the mixture in an agitated condition at 1,200 rpm.

After 19 hours, the reaction mixture was then cooled and quantitative analysis of the products of the reaction was carried out. The diphenylfuchsone obtained and the residual benzophenone were subjected to quantitative analysis by gaseous phase chromatography.

The results obtained were as follows:
(a) $RR_{FUCHSONE}=26.2\%$
(b) $TT_{BENZOPHENONE}=28.6\%$
(c) $RT_{FUCHSONE}=91.5\%$

EXAMPLE 2

The procedure of Example 1 was repeated, except that the reaction temperature was 80° C. instead of 70° C.

After 4 hours of reaction, the results obtained were as follows:
(a) $RR_{FUCHSONE}=20.8\%$
(b) $TT_{BENZOPHENONE}=20.8\%$
(c) $RT_{FUCHSONE}=100\%$ After 5 hours of reaction, the results obtained were as follows:

(a') $RR_{FUCHSONE}=22.6\%$
(b') $TT_{BENZOPHENONE}=22.6\%$
(c') $RT_{FUCHSONE}=100\%$

EXAMPLE 3

The following reagents were introduced into the apparatus described in Example 1:
(i) 19.8 g (0.20 mole) of phenol,
(ii) 18.2 g (0.10 mole) of benzophenoNe, and
(iii) 0.75 g (0.005 mole) of trifluoromethanesulfonic acid, $CF_3SO_3H$.

The reaction mixture was heated to a temperature of 80° C., while being maintained in an agitated condition at 1,200 rpm.

The procedure of Example 1 was thus repeated, except that the reaction temperature was 150° C. instead of 70° C.

After 1 hour of reaction, the results obtained were as follows:
(a) $RR_{FUCHSONE}=3.8\%$
(b) $TT_{BENZOPHENONE}=4.6\%$
(c) $RT_{FUCHSONE}=83\%$ After 6 hours of reaction, the results obtained were as follows:
(a') $RR_{FUCHSONE}=3.8\%$
(b') $TT_{BENZOPHENONE}=6.5\%$
(c') $RT_{FUCHSONE}=58.5\%$

EXAMPLE 4

The following reagents were introduced into the apparatus described in Example 1:
(i) 9.4 g (0.10 mole) of phenol,
(ii) 18.2 g (0.10 mole) of benzophenone, and
(iii) 7.5 g (0.05 mole) of trifluoromethanesulfonic acid, $CF_3SO_3H$.

The reaction mixture was heated to a temperature of 80° C., while being maintained in an agitated condition at 1,200 rpm.

After 4 hours of reaction, the results obtained were as follows:
(a) $RR_{FUCHSONE}=17\%$
(b) $TT_{BENZOPHENONE}=17\%$
(c) $RT_{FUCHSONE}=100\%$ An additional 0.05 mole of trifluoromethanesulfonic acid, $CF_3SO_3H$, was then added.

After 6 hours, 45 minutes, the results obtained were as follows:
(a') $RR_{FUCHSONE}=29\%$
(b') $TT_{BENZOPHENONE}=29\%$
(c') $RT_{FUCHSONE}=100\%$

EXAMPLE 5

The procedure of Example 1 was repeated, except that 70% perchloric acid was used, in the same amount.

The reaction temperature was also 70° C.

After 28 hours of reaction, the results obtained were as follows:
(a) $RR_{FUCHSONE}=5.9\%$
(b) $TT_{BENZOPHENONE}=6.0\%$
(c) $RT_{FUCHSONE}=98\%$

EXAMPLE 6

The following reagents were introduced into the apparatus described in Example 1:

(i) 19.8 g (0.2 mole) of phenol, (ii) 18.2 g (0.1 mole) of benzophenone, and (iii) 4.8 g (0.05 mole) of methanesulfonic acid.

The reaction mixture was heated to the selected reaction temperature of 150° C., while being maintained in an agitated condition at 1,200 rpm.

After 5 hours of reaction, the results obtained were as follows:

(a) $RR_{FUCHSONE}=8\%$ (b) $TT_{BENZOPHENONE}=15\%$ (c) $RT_{FUCHSONE}=53\%$

EXAMPLE 7

The procedure of Example 6 was repeated, but with methanesulfonic acid being replaced by benzenesulfonic acid.

The selected reaction temperature was 120° C.

After 4 hours, 30 minutes, of reaction, the results obtained were as follows:

(a) $RR_{FUCHSONE}=1.5\%$ (b) $TT_{BENZOPHENONE}=2.4\%$ (c) $RT_{FUCHSONE}=63\%$

EXAMPLE 8

The procedure of Example 6 was repeated, except that methanesulfonic acid was replaced by pyrophosphoric acid.

After 3 hours of reaction, the results obtained were as follows:

(a) $RR_{FUCHSONE}=1\%$ (b) $TT_{BENZOPHENONE}=1\%$ (c) $RT_{FUCHSONE}=100\%$

EXAMPLE 9

The following reagents were introduced into the apparatus described in Example 1:

(i) 19.8 g (0.2 mole) of phenol, (ii) 9.2 g (0.1 mole) of benzophenone, and (iii) 1.1 g (0.014 mole) of hydrobromic acid.

The hydrobromic acid was introduced in gaseous form by bubbling 1.1 g thereof into the reaction mixture over a period of 20 minutes.

The reaction temperature selected was 75° C.

After 6 hours of reaction, the results obtained were as follows:

(a) $RR_{FUCHSONE}=2.9\%$ (b) $TT_{BENZOPHENONE}=3.2\%$ (c) $RT_{FUCHSONE}=90.6\%$

EXAMPLE 10

The procedure of Example 9 was repeated, but with hydrobromic acid being replaced by gaseous hydrochloric acid, by bubbling, throughout the duration of the test. The operation was carried out in the presence of 1 ml of water.

After 16 hours of reaction, the results obtained were as follows:

(a) $RR_{FUCHSONE}=1\%$ (b) $TT_{BENZOPHENONE}=1\%$ (c) $RT_{FUCHSONE}=100\%$

EXAMPLE 11

The following reagents were introduced into a 100 ml metallic reactor:

(i) 4.7 g (0.050 mole) of phenol, (ii) 9.1 g (0.05 mole) of benzophenone, and (iii) 20 g (1.00 mole) of anhydrous hydrofluoric acid.

The reactor was sealed and the reaction mixture was heated to the selected temperature of 80 ° C., while maintaining it in an agitated condition.

After 4 hours of reaction, the mixture was transferred into 100 ml of water. Extraction was conducted by means of dichloromethane. The organic phase obtained was washed with water until its pH was 5. The aqueous and organic phases were separated.

Quantitative analysis in respect of benzophenone and fuchsone was then carried out. The results obtained were as follows:

(a) $RR_{FUCHSONE}=31\%$ (b) $TT_{BENZOPHENONE}=36\%$ (c) $RT_{FUCHSONE}=86\%$

EXAMPLE 12

The procedure of Example 11 was repeated, except that the reaction temperature was 120° C. instead of 80° C.

After 4 hours of reaction, the results obtained were as follows:

(a) $RR_{FUCHSONE}=10\%$ (b) $TT_{BENZOPHENONE}=18\%$ (c) $RT_{FUCHSONE}=55.5\%$

EXAMPLE 13

The following reagents were introduced into the apparatus described in Example 1:

(i) 18.8 g (0.2 mole) of phenol, (ii) 18.2 g (0.1 mole) of benzophenone, and (iii) 6.65 g (0.5 mole) of aluminum chloride, $AlCl_3$.

The reaction mixture was heated to a temperature of 80° C., while being maintained in an agitated condition.

After 4 hours of reaction, quantitative analysis was carried out in respect of the products formed after acid hydrolysis using 100 ml of an aqueous 1.2N hydrochloric solution, followed by extraction of the organic products by means of ethyl acetate.

The results obtained were as follows:

(a) $RR_{FUCHSONE}=9\%$ (b) $TT_{BENZOPHENONE}=16\%$ (c) $RT_{FUCHSONE}=56\%$

EXAMPLE 14

The procedure of Example 13 was repeated, except that aluminum chloride was replaced by titanium chloride, $TiCl_4$.

After 3 hours of reaction, the results obtained were as follows:

(a) $RR_{FUCHSONE}=1.0\%$ (b) $TT_{BENZOPHENONE}=6.5\%$ (c) $RT_{FUCHSONE}=15.5\%$

EXAMPLE 16

The following reagents were introduced into the apparatus described in Example 1:

(i) 9.4 g (0.20 mole) of phenol, (ii) 9.1 g (0.10 mole) of benzophenone, and (iii) 2.0 g of zeolite US-Y.

The zeolite US-Y was a zeolite marketed by TOSOH, having an Si/Al molar ratio of 6.0.

The reaction temperature selected was 150° C.

After 5 hours of reaction, the results obtained were as follows:

(a) $RR_{FUCHSONE}=2\%$ (b) $TT_{BENZOPHENONE}=2\%$ (c) $RT_{FUCHSONE}=100\%$

EXAMPLE 16

The procedure of Example 15 was repeated, except that the zeolite US-Y was replaced by a clay KO of type VOLCLAY.

After 5 hours, 30 minutes, of reaction, the results obtained were as follows:

(a) $RR_{FUCHSONE}=2\%$ (b) $TT_{BENZOPHENONE}=2\%$ (c) $RT_{FUCHSONE}=100\%$

EXAMPLE 17

The following reagents were introduced into the apparatus described in Example 1:

(i) 0.20 mole of phenol, (ii) 0.10 mole of benzophenone, and (iii) 0.05 mole equivalent $H^+$ of a sulfonic resin.

The sulfonic resin was a perfluorinated resin prepared from a copolymer of tetrafluoroethylene and perfluoro-[2-(fluorosulfonylethoxy)-propyl] vinyl ether which is marketed under the trademark NAFION®.

The reaction temperature was 145° C.

After 3 hours of reaction, the following results were obtained:

(a) $RR_{FUCHSONE}=14\%$ (b) $TT_{BENZOPHENONE}=16.8\%$ (c) $RT_{FUCHSONE}=83.5\%$

EXAMPLE 18

The following reagents were introduced into the apparatus described in Example 1:

(i) 9.4 g (0.1 mole) of phenol, (ii) 2.14 G (0.01 mole) of 4,4'-dihydroxybenzophenone, and (iii) 3.1 g (0.02 mole) of trifluoromethanesulfonic acid, $CF_3SO_3H$.

The reaction temperature was 150° C.

After 4 hours of reaction, the following results were obtained:

(a) $RR_{ROSOLIC\ ACID}=5\%$ (b) $TT_{KETONE}=15\%$ (c) $RT_{ROSOLIC\ ACID}=33.5\%$

EXAMPLE 19

The following reagents were introduced into the apparatus described in Example 1:

(i) 21.6 g (0.2 mole) of ortho-cresol, (ii) 18.2 g (0.1 mole) of benzophenone, and (iii) 7.5 g (0.05 mole) of trifluoromethanesulfonic acid, $CF_3SO_3H$.

The reaction temperature was 80° C.

After 3 hours of reaction, the following results were obtained:

(a) $RR_{METHYLFUCHSONE}=25\%$ (b) $TT_{BENZOPHENONE}=26.3\%$ (c) $RT_{METHYLFUCHSONE}=95\%$

EXAMPLE 20

The following reagents were introduced into the apparatus described in Example 1:

(i) 0.22 mole of phenol, (ii) 0.02 mole of benzophenone, and (iii) 0.20 mole of hydrated trifluoromethanesulfonic acid, $CF_3SO_3H$, $H_2O$.

The reaction temperature was 120° C.

After 4 hours of reaction, the following results were obtained:

(a) $RR_{FUCHSONE}=66\%$ (b) $TT_{BENZOPHENONE}=84.5\%$ (c) $RT_{FUCHSONE}=78\%$

EXAMPLE 21

The following reagents were introduced the apparatus described in Example 1:

(i) 23.5 g (0.25 mole) of phenol, (ii) 4.55 g (0.025 mole) of benzophenone, (iii) 7.5 g (0.05 mole) of trifluoromethanesulfonic acid, and (iv) p-xylene in an amount such that the total reaction volume was 50 ml.

The reaction mixture was heated to a temperature of 110° C., while maintaining it in an agitated condition at 1,200 rpm.

After 4 hours, the reaction mixture was then cooled and quantitative analysis of the reaction products was carried out.

The results obtained were as follows:

(a) $RR_{FUCHSONE}=68\%$ (b) $TT_{BENZOPHENONE}=84.5\%$ (c) $RT_{FUCHSONE}=80.5\%$

EXAMPLE 22

The following reagents were introduced into the apparatus described in Example 1:

(i) 4.7 g (0.05 mole) of phenol, (ii) 0.91 g (0.005 mole) of benzophenone, (iii) 4.8 g (0.05 mole) of methanesulfonic acid, and (iv) 30 ml of methylcyclohexane.

The reaction mixture was heated to 80° C., while maintaining it in an agitated condition at 1,200 rpm. The medium comprised two phases.

After 5 hours, the reaction mixture was then cooled and, in each phase, quantitative analysis of the reaction products was conducted.

The results obtained were as follows:

(a) $RR_{FUCHSONE}=15\%$ (b) $TT_{BENZOPHENONE}=20\%$ (c) $RT_{FUCHSONE}=75\%$

EXAMPLE 23

The procedure of Example 22 was repeated, except that the methylcyclohexane was replaced by the same volume of cyclohexane and the water was removed by azeotropic distillation.

The results obtained were as follows:

(a) $RR_{FUCHSONE}=24\%$ (b) $TT_{BENZOPHENONE}=28\%$ (c) $RT_{FUCHSONE}=85.5\%$

EXAMPLE 24

The following reagents were introduced into the apparatus described in Example 1:

(i) 56.4 g (0.6 mole) of phenol, (ii) 10.92 g (0.06 mole) of benzophenone, and (iii) 46.06 g (0.48 mole) of methanesulfonic acid.

The reaction mixture was heated to a temperature of 100° C. over a period of 7 hours, while being maintained in an agitated condition at 1,200 rpm.

The reaction mixture was then cooled and 50 ml of water and 100 ml of isopropyl ether were added. The ether phase was decanted and washed 3 times with 50 ml of water.

The following were determined in the organic ether phase:

(a) FUCHSONE=0.0347 mole (RR=58.3%)

(b) BENZOPHENONE=0.0240 mole (TT=59.8%)

EXAMPLES 25 TO 52

EXAMPLE 25

The following reagents were introduced into a 50 ml glass round-bottom flask provided with a central agitation system, a condenser and a thermometer:

(i) 23.5 g (0.25 mole) of phenol, (ii) 4.55 g (0.025 mole) of benzophenone, (iii) 7.9 g (0.05 mole) of benzenesulfonic acid, and (iv) 0.621 g (0.005 mole) of benzylmercaptan.

The reaction mixture was heated to the selected reaction temperature of 110° C., while being maintained in an agitated condition at 1,200 rpm.

After 4 hours, the reaction mixture was cooled and quantitative analysis was carried out in respect of the products of the reaction. Diphenylfuchsone and residual benzophenone were subjected to quantitative analysis by gaseous phase chromatography.

The results obtained were as follows:

(a) $RR_{FUCHSONE}=57.6\%$ (b) $TT_{BENZOPHENONE}=62\%$ (c) $RT_{FUCHSONE}=92.9\%$

The same test, when carried out using benzylmercaptan, gave the following results, after 4 hours of reaction at 110° C.:

(a') $RR_{FUCHSONE}=14\%$ (b') $TT_{BENZOPHENONE}=15.2\%$ (c') $RT_{FUCHSONE}=92.1\%$

The Figure of Drawing is a graph illustrating two curves in respect of the variation in the yield (RR expressed in %) depending on the duration of the reaction (expressed in hours), one in the presence of benzylmercaptan (B) and the other in the absence of thiol (A).

It will be appreciated that the presence of a thiol made it possible to considerably increase the rate of formation of the fuchsone.

EXAMPLE 26

The following reagents were introduced into a 50 ml glass round-bottom flask provided with a central agitation system, a condenser and a thermometer:

(i) 23.5 g (0.25 mole) of phenol, (ii) 4.55 g (0.025 mole) of benzophenone, (iii) 7.5 g (0.05 mole) of trifluoromethanesulfonic acid, and (iv) 0.621 g (0.005 mole) of benzylmercaptan.

The reaction mixture was heated to the selected reaction temperature of 80° C., while maintained in an agitated condition at 1,200 rpm.

After 4 hours, the reaction mixture was cooled and quantitative analysis was carried out in respect of the products of the reaction. Diphenylfuchsone and residual benzophenone were determined by quantitative analysis by gaseous phase chromatography.

The results obtained were as follows:

(a) $RR_{FUCHSONE}=94.8\%$ (b) $TT_{BENZOPHENONE}=99.2\%$ (c) $RT_{FUCHSONE}=95.6\%$

The same experiments when carried out without benzylmercaptan, gave the following results after 4 hours of reaction at 80° C.:

(a') $RR_{FUCHSONE}=63.2\%$ (b') $TT_{BENZOPHENONE}=64.8\%$ (c') $RT_{FUCHSONE}=97.5\%$

EXAMPLE 27

The following reagents were introduced into a 50 ml glass round-bottom flask provided with a central agitation system, a condenser and a thermometer:

(i) 23.5 g (0.25 mole) of phenol, (ii) 4.55 g (0.025 mole) of benzophenone, (iii) 7.9 g (0.05 mole) of benzenesulfonic acid, and (iv) 0.801 g (0.005 mole) of 1-nonylmercaptan.

The reaction mixture was heated to the selected reaction temperature of 110° C., while maintained in an agitated condition at 1,200 rpm.

After 4 hours, the reaction mixture was cooled and quantitative analysis was carried out in respect of the products of the reaction. Diphenylfuchsone and residual benzophenone were determined by quantitative analysis by gaseous phase chromatography.

The results obtained were as follows:

(a) $RR_{FUCHSONE}=62\%$ (b) $TT_{BENZOPHENONE}=67.6\%$ (c) $RT_{FUCHSONE}=91.7\%$

The same experiment, when carried out without 1-nonylmercaptan, gave the following results after 4 hours of reaction at 110° C.:

(a') $RR_{FUCHSONE}=14\%$ (b') $TT_{BENZOPHENONE}=15.2\%$ (c') $RT_{FUCHSONE}=92.1\%$

EXAMPLE 28

The following reagents were introduced into a 250 ml glass round-bottom flask provided with a central agitation system, a condenser and a thermometer:

(i) 94 g (1 mole) of phenol, (ii) 18.2 g (0.1 mole) of benzophenone, (iii) 76.8 g (0.8 mole) of methanesulfonic acid, and (iv) 1.8 g (0.02 mole) of 1-butane thiol.

The reaction mixture was heated to the selected reaction temperature of 80° C., while being maintained in an agitated condition at 1,200 rpm.

After 7 hours, the reaction mixture was cooled and quantitative analysis of the products of the reaction was carried out. Diphenylfuchsone and residual benzophenone were determined by quantitative analysis by gaseous phase chromatography.

The results obtained were as follows:

(a) $RR_{FUCHSONE}$=96.5%

(b) $TT_{BENZOPHENONE}$=97.4%

(c) $RT_{FUCHSONE}$=99.1%

EXAMPLE 29

The following reagents were introduced into a 100 ml glass round-bottom flask provided with a central agitation system, a condenser and a thermometer:

(i) 28.2 g (0.3 mole) of phenol, (ii) 5.46 g (0.03 mole) of benzophenone, (iii) 23.04 g (0.24 mole) of methanesulfonic acid, and (iv) 0.984 g (0.006 mole) of sodium 2-mercaptoethane sulfonate.

The reaction mixture was heated selected reaction temperature of 110° C., while being maintained in an agitated condition at 1,200 rpm.

After 4 hours, the reaction mixture was cooled and quantitative analysis of the products of the reaction was carried out. Diphenylfuchsone and residual benzophenone were determined by quantitative analysis by gaseous phase chromatography.

The results obtained were as follows:

(a) $RR_{FUCHSONE}$=83.7%

(b) $TT_{BENZOPHENONE}$=99%

(c) $RT_{FUCHSONE}$=84.5%

The same experiment was carried out without the thiol. The results obtained were as follows:

(a') $RR_{FUCHSONE}$=46.3%

(b') $TT_{BENZOPHENONE}$=47%

(c') $RT_{FUCHSONE}$=98.5%

EXAMPLE 30

The procedure of Example 29 was repeated, except that 0.246 g (0.0015 mole) of sodium 2-mercaptoethane sulfonate was used instead of 0.984 g (0.006 mole).

After 4 hours at 110° C., the results obtained were as follows:

(a) $RR_{FUCHSONE}$=83.6%

(b) $TT_{BENZOPHENONE}$=91%

(c) $RT_{FUCHSONE}$=94.8%

EXAMPLE 31

The procedure of Example 29 was repeated, except that 0.025 g (0.00015 mole) of sodium 2-mercaptoethane sulfonate was used instead of 0.984 g (0.006 mole).

After 4 hours at 110° C., the results obtained were as follows:

(a) $RR_{FUCHSONE}$=65%

(b) $TT_{BENZOPHENONE}$=65.7%

(c) $RT_{FUCHSONE}$=98.9%

EXAMPLE 32

The following reagents were introduced into a reactor provided with a central agitation system, a condenser and a thermometer:

(i) 8.04 g (0.085 mole) of phenol, (ii) 1.55 g (0.0085 mole) of benzophenone, (iii) 1.67 g (0.0085 mole equivalent H$^+$) of resin BAYER K2431, and (iv) 0.212 g (0.0017 mole) of benzylmercaptan.

The resin BAYER K2431 was a macroporous resin having a polystyrene skeleton bearing sulfonic groups, with a concentration of acid sites of 5.1 milliequivalents of H$^+$ per gram of dry polymer.

The reaction mixture was heated to the selected temperature of 145° C., while being maintained in an agitated condition at 1,200 rpm. After 4 hours of reaction, the resin was separated from the reaction mixture by filtration over fritted glass and washed with 20 ml of phenol at 80° C. The filtrate and the washing phase were combined.

The resin was agitated for 1 hour at ambient temperature with a 50/50 mixture of water and ethyl acetate and then filtered. The organic phase was separated by settling.

The diphenylfuchsone and residual benzophenone which were contained in the phenolic phase and in the ethyl acetate phase were determined by quantitative analysis by gaseous phase chromatography.

The results obtained were as follows:

(a) $RR_{FUCHSONE}$=11.8%

(b) $TT_{BENZOPHENONE}$=14%

(c) $RT_{FUCHSONE}$=84.3%

The same experiment, when carried out without benzylmercaptan, after 4 hours of reaction at a temperature of 145° C., gave the following results:

(a') $RR_{FUCHSONE}$=6.2%

(b') $TT_{BENZOPHENONE}$=6.2%

(c') $RT_{FUCHSONE}$=100%

EXAMPLE 33

The following reagents were introduced into a reactor provided with a central agitation system, a condenser and a thermometer:

(i) 8.04 g (0.085 mole) of phenol, (ii) 1.55 g (0.0085 mole) of benzophenone, (iii) 1.67 g (0.0085 equivalent H$^+$) of resin BAYER K2431, and (iv) 0.274 g (0.0017 mole) of 1-nonylmercaptan.

The reaction mixture was heated to the selected temperature of 145° C., while being maintained in an agitated condition at 1,200 rpm.

After 4 hours of reaction, the resin was separated from the reaction mixture by filtration over fritted glass and washed with 20 ml of phenol at 80° C. The filtrate and the washing phase were combined.

The resin was agitated for 1 hours at ambient temperature with a 50/50 mixture of water and ethyl acetate and then filtered. The organic phase was separated by settling.

The diphenylfuchsone and residual benzophenone which were contained in the phenolic phase and in the ethyl acetate phase were determined by quantitative analysis by gaseous phase chromatography.

The results obtained were as follows:

(a) $RR_{FUCHSONE}$=11.6%

(b) $TT_{BENZOPHENONE}$=17.8%

(c) $RT_{FUCHSONE}$=65.17%

The same experiment, when carried out without 1-nonylmercaptan, after 4 hours of reaction at a temperature of 145° C., gave the following results:

(a') $RR_{FUCHSONE}$=6.2%

(b') $TT_{BENZOPHENONE}$=6.2%

(c') $RT_{FUCHSONE}$=100%

EXAMPLE 34

The following reagents were introduced into a 50 ml reactor provided with a central agitation system, a thermometer and a condenser:

(i) 0.47 g (0.005 mole) of phenol, (ii) 0.91 g (0.005 mole) of benzophenone, (iii) 8.9 g (0.05 mole) of orthophosphoric acid, and (iv) 0.164 g (0.001 mole) of sodium 2-mercaptoethane sulfonate.

The reaction mixture was heated to the selected temperature of 80° C., while being maintained in an agitated condition at 1,200 rpm.

After 5 hours of reaction, the reaction mixture was cooled and quantitative analysis of the products of the reaction was carried out. Diphenylfuchsone and residual benzophenone were determined by quantitative analysis by high-performance liquid chromatography.

The results obtained were as follows:

(a) $RR_{FUCHSONE}$=29.6%

(b) $TT_{BENZOPHENONE}$=35.6%

(c) $RT_{FUCHSONE}$=83.1%

The same experiment, when carried out without the 2-mercaptoethane thiol, after 5 hours of reaction at 80° C., gave the following results:

(a') $RR_{FUCHSONE}$=4%

(b') $TT_{BENZOPHENONE}$=4%

(c') $RT_{FUCHSONE}$=100%

EXAMPLE 35

The following reagents were introduced into a 50 ml reactor provided with a central agitation system, a thermometer and a condenser:

(i) 0.47 g (0.005 mole) of phenol, (ii) 0.91 g (0.005 mole) of benzophenone, (iii) 8.9 g (0.05 mole) of orthophosphoric acid, and (iv) 0.164 g (0.001 mole) of sodium 2-mercaptoethane sulfonate.

The reaction mixture was heated to the selected temperature of 110° C., while being maintained in an agitated condition at 1,200 rpm.

After 5 hours of reaction, the reaction mixture was cooled and quantitative analysis of the products of the reaction was carried out. Diphenylfuchsone and residual benzophenone were determined by quantitative analysis by high-performance liquid chromatography.

The results obtained were as follows:

(a) $RR_{FUCHSONE}$=30.4%

(b) $TT_{BENZOPHENONE}$=49.6%

(c) $RT_{FUCHSONE}$=61.3%

The same experiment, when carried out without the 2-mercaptoethane thiol, after 5 hours of reaction at 110° C., gave the following results:

(a') $RR_{FUCHSONE}$=3%

(b') $TT_{BENZOPHENONE}$=10%

(c') $RT_{FUCHSONE}$=30%

EXAMPLES 36 TO 49

The following reagents were introduced into a 100 ml glass round-bottom flask provided with a central agitation system, a condenser and a thermometer:

(i) 28.2 g (0.3 mole) of phenol, and (ii) 23.04 g (0.24 mole) of methanesulfonic acid.

Benzophenone and sodium 2-mercaptoethane sulfonate were added in the molar ratios reported in Table I.

The reaction mixtures were heated to the selected temperatures, while being maintained in an agitated condition at 1,200 rpm.

At the end of the reaction, the reaction mixtures were cooled and quantitative analysis operations in respect of the reaction were carried out.

The results and the operating conditions of each experiment are reported in Table I:

TABLE I

| Example | Reactants (number of moles) | | | | Reaction T °C. (°C.) | Duration hours | Yields | | | Duration hours | Yields | | |
|---|---|---|---|---|---|---|---|---|---|---|---|---|---|
| | Phenol | Ph₂CO | MeSo₃H | Thiol | | | TT Ph₂CO | RR fuchsone | RT fuchsone | | TT Ph₂CO | RR fuchsone | RT fuchsone |
| 36 | 10 | 1 | 8 | 0.2 | 80 | 4 | 96.4 | 75.8 | 78.6 | 5 | 97.6 | 79.6 | 81.6 |
| 37 | 10 | 1 | 8 | 0.05 | 80 | 4 | 80 | 75 | 93.8 | 7 | 88.7 | 86 | 97 |
| 38 | 10 | 1 | 8 | 0.05 | 140 | 4 | 95 | 88 | 92.6 | — | — | — | — |
| 39 | 10 | 1.5 | 8 | 0.05 | 110 | 5 | 76.9 | 76 | 98.8 | 7 | 80.7 | 78.4 | 97.2 |
| 40 | 10 | 1 | 8 | 0.2 | 110 | 4 | 99 | 83.7 | 84.5 | — | — | — | — |
| 41 | 10 | 0.5 | 8 | 0 | 110 | 4 | 56.6 | 55.3 | 97.7 | 7 | 74 | 70.7 | 95.5 |
| 42 | 10 | 1 | 8 | 0 | 140 | 5 | 84.8 | 73 | 86.1 | 7 | 89.7 | 77.8 | 86.7 |
| 43 | 10 | 1 | 8 | 0 | 110 | 4 | 45.2 | 43.7 | 96.6 | 7 | 60.5 | 57.8 | 95.5 |
| 44 | 10 | 1 | 8 | 0 | 110 | 4 | 43.6 | 41.3 | 94.8 | 7 | 59 | 58.7 | 99.4 |
| 45 | 10 | 2 | 8 | 0 | 110 | 4 | 34 | 33.5 | 98.5 | 7 | 44 | 43.5 | 98.9 |
| 46 | 10 | 2 | 8 | 0.005 | 110 | 4 | 41 | 40.5 | 98.8 | 7 | 50 | 50 | 100 |
| 47 | 10 | 2 | 8 | 0.05 | 110 | 4 | 59.5 | 58 | 97.5 | 7 | 66.5 | 65 | 97.7 |
| 48 | 10 | 2 | 8 | 0.1 | 110 | 4 | 67 | 64.5 | 96.3 | 7 | 74.5 | 67.5 | 90.6 |
| 49 | 10 | 3 | 8 | 0 | 110 | 4 | 22.3 | 22.3 | 100 | 7 | 30 | 30 | 100 |

EXAMPLE 50

The following reagents were introduced into an apparatus as previously described:

(i) 4.7 g (0.05 mole) of phenol, (ii) 0.91 g (0.005 mole) of benzophenone, (iii) 4.8 g (0.05 mole) of methanesulfonic acid, (iv) 0.164 g (0.001 mole) of sodium 2-mercaptoethane sulfonate, and (v) 30 ml of cyclohexane.

The mixture was heated under reflux for a period of 5 hours, with the water formed being azeotropically removed.

The solution was then cooled, 10 ml of water were added and extraction was carried out using ethyl acetate.

The results obtained were as follows:

(a) $TT_{BENZOPHENONE}=100\%$ (b) $RR_{FUCHSONE}=96\%$

EXAMPLE 51

The following reagents were introduced into the apparatus described in Example 1:

(i) 4.7 g (0.05 mole) of phenol, (ii) 9.1 g (0.05 mole) of benzophenone, (iii) 89 g (0.5 mole) of pyrophosphoric acid, and (iv) 1.64 g (0.01 mole) of sodium 2-mercaptoethane sulfonate.

That mixture was heated to a temperature of 110° C. during a period of 5 hours with agitation at 1,200 rpm.

The reaction medium was the cooled and quantitative analysis was carried out in respect of the residual benzophenone and the diphenylfuchsone formed.

The results obtained were as follows:

(a) $TT_{BENZOPHENONE}=50\%$ (b) $RR_{FUCHSONE}=31\%$

EXAMPLES 52 to 66

Examples 52 to 66 illustrate the preparation of a para-hydroxylated compound by oxidation of a p-fuchsone.

In said Examples, the following abbreviations have the following definitions:

$$TT_{H_2O_2} = \frac{\text{number of moles of hydrogen peroxide converted}}{\text{number of moles of hydrogen peroxide introduced}} \%$$

$$TT_{FUCHSONE} = \frac{\text{number of moles of fuchsone converted}}{\text{number of moles of fuchsone introduced}} \%$$

$$RR_{HQ/FUCHSONE} = \frac{\text{number of moles of hydroquinone formed}}{\text{number of moles of fuchsone introduced}} \%$$

$$RT_{HQ/FUCHSONE} = \frac{\text{number of moles of hydroquinone formed}}{\text{number of moles of fuchsone converted}} \%$$

$$RT_{PC/FUCHSONE} = \frac{\text{number of moles of pyrocatechin formed}}{\text{number of moles of fuchsone converted}} \%$$

$$RT_{HQ/H_2O_2} = \frac{\text{number of moles of hydroquinone formed}}{\text{number of moles of H}_2\text{O}_2 \text{ transformed}} \%$$

$$RT_{PC/H_2O_2} = \frac{\text{number of moles of pyrocatechin formed}}{\text{number of moles of H}_2\text{O}_2 \text{ converted}} \%$$

EXAMPLE 52

The following reagents were introduced into a 25 ml glass round-bottom flask provided with a central agitation system, a condenser, a dropping funnel and a thermometer:

(i) 0.774 g (0.003 mole) of dipenylfuchsone, (ii) 7.7 ml of acetonitrile, and (iii) 18 mg (0.12 mmole) of 70% perchloric acid.

The reaction mixture was heated to the selected reaction temperature of 30° C., while being maintained in an agitated condition.

An amount of 0.146 g (0.003 mole) of hydrogen peroxide in the form of a 70.5% aqueous solution was introduced by means of the dropping funnel over a period of 2 minutes. The temperature autogenously increased to 60° C.

The reaction mixture was then cooled and quantitative analysis of the reaction products was carried out. The residual hydrogen peroxide was determined by quantitative analysis by iodometry and the diphenols formed were determined quantitative analysis by high-performance liquid chromatography.

After 1 hour of reaction, the results obtained were as follows:

(a) $TT_{FUCHSONE}=100\%$ (b) $RR_{HYDROQUINONE/FUCHSONE}=96.5\%$ (c) $RT_{HYDROQUINONE/FUCHSONE}=96.5\%$

Benzophenone was recovered at a recovery rate of 96%.

EXAMPLE 53

This Example describes the preparation of hydroquinone via reaction of diphenylfuchsone obtained from phenol and benzophenone with hydrogen peroxide in the presence of perchloric acid.

The following reagents were introduced into a reactor with controlled agitation and with thermal regulation:

(i) 19.8 g (0.2 mole) of phenol, (ii) 18.2 g (0.1 mole) of benzophenone, and (iii) 7.5 g (0.05 mole) of anhydrous trifluoromethanesulfonic acid, $CF_3SO_3H$.

The reaction mixture was headed to the selected reaction temperature of 70° C., while being maintained in an agitated condition.

After 19 hours, the reaction mixture was then cooled.

100 ml of ethyl acetate were added to the reaction medium. The organic phase was washed with 3×20 ml of water and then 1×30 ml of a saturated aqueous solution of $NaHCO_3$. Washing was then effected using 2×20 ml of water.

The aqueous and organic phases were separated.

The organic phase was dried over $MgSO_4$ for a period of 1 hour. Filtration was carried out and $MgSO_4$ was washed with 20 ml of ethyl acetate which was combined with the organic phase.

The ethyl acetate was evaporated under a reduced pressure of 25 mm of mercury.

In the medium, quantitative analysis was conducted as follows:

(a) benzophenone=13 g (71.4 mmole) [$TT_{BENZOPHENONE}=28.6\%$]

(b) fuchsone=6.75 g (26.2 mmole) [$RR_{FUCHSONE}=26.2\%$]

That reaction medium was placed in a reactor.

Also introduced was an amount of hydrogen peroxide corresponding to the stoichiometric amount in the form of a 71% aqueous solution of hydrogen peroxide (namely, 26.2 mmole of pure $H_2O_2$).

After 5 hours at 25° C., the $RR_{HYDROQUINONE/FUCHSONE}$ yield was 33%.

An amount of 0.2 mmole of 70% by weight perchloric acid was added.

After 15 minutes, quantitative analysis was carried out in respect of the hydroquinone formed, using gaseous phase chromatography:

(a') $TT_{FUCHSONE}=100\%$ (b') $RR_{HYDROQUINONE/FUCHSONE}=97.8\%$

The rate of recovery of benzophenone was 97.7%.

EXAMPLE 54

This Example relates to the preparation of methylhydroquinone.

The following reagents were introduced into the reactor which included controlled agitation and thermal regulation:

(i) 21.6 g (0.200 mole) of 0-cresol, (ii) 18.2 g (0.100 mole) of benzophenone, and (iii) 7.8 g (0.052 mole) of anhydrous trifluoromethanesulfonic acid, $CF_3SO_3H$.

The mixture was heated at 80° C. for a period of 3 hours.

An amount of 140 ml of ethyl acetate was added to the reaction mixture. The organic phase was washed with 2×30 ml of $H_2O$ and then 3×30 ml of a saturated aqueous solution of $NaHCO_3$. Washing was then carried out using 2×30 ml of $H_2O$.

The aqueous and organic phases were separated.

The organic phase was dried over $MgSO_4$ for a period of 1 hour. Filtration was carried out and $MgSO_4$ was washed with 20 ml of ethyl acetate which was combined with the organic phase.

The ethyl acetate was evaporated under a reduced pressure of 25 mm of mercury (weight obtained=38.6 g).

On that medium, quantitative analysis was conducted:

(a) benzophenone=13.41 g (73.7 mmole) [$TT_{BENZOPHENONE}=26.3\%$]

(b) diphenylmethylfuchsone=6.8 g (25 mmole) [$RR_{FUCHSONE}=25\%$]

(c) o-cresol=20.1 g.

This reaction medium was placed into a reactor and 37 mg (0.26 mmole) of 70% by weight perchloric acid were added. The reaction mixture was heated to 30°–35° C. and introduced therein was 1.225 g of a 71% aqueous solution of hydrogen peroxide (i.e., 25.5 mmole of pure $H_2O_2$).

After 1 hour, 30 minutes, the conversion of $H_2O_2$ was 90%.

Quantitative analysis by means of gaseous phase chromatography was carried out in respect of the methylhydroquinone formed, namely, 2.85 g (23 mmole), which corresponded to an $RR_{METHYLHYDROQUINONE/FUCHSONE}$ yield of 92.5%.

The rate of recovery of the benzophenone was 99.1%.

EXAMPLE 55 AND 56

These Examples employed phenol, benzophenone, diphenylfuchsone and perchloric acid in the following molar ratios: 4/4/1/0.015.

The reaction medium was heated to a temperature of 75° C. and an aqueous solution of hydrogen peroxide was poured therein, while maintaining the temperature at 75° C.

After one hour, the results obtained were as follows:

TABLE II

| Example | $H_2O_2$/ fuchsone molar ratio | TT FUCHSONE | TT $H_2O_2$ | % of benzophenone recovered | $RT_{HQ}$ | $RT_{PC}$ |
|---|---|---|---|---|---|---|
| 55 | 1.04 | 92.5 | 100 | 91 | 90 | 1 |
| 56 | 1.32 | 98.0 | 100 | 95 | 86 | 5 |

EXAMPLE 57

The following reagents were introduced into a 100 ml glass round-bottom flask provided with a central agitation system, a condenser, a dropping funnel and a thermometer:

(i) 19.8 g (0.2 mole) of phenol, (ii) 18.2 g (0.1 mole) of benzophenone, and (iii) 7.5 g (0.05 mole) of trifluoromethanesulfonic acid, $CF_3SO_3H$.

The reaction mixture was heated to the selected reaction temperature of 80° C., while being maintained in an agitated condition.

After 22 hours, the reaction mixture was then cooled and quantitative analysis of the products of the reaction was carried out. The diphenylfuchsone was determined by quantitative analysis by gaseous phase chromatography.

The results obtained were as follows:

(a) benzophenone=12.55 g (69 mmole) [$TT_{BENZOPHENONE}=31\%$]

(b) fuchsone=7.87 g (30.5 mmole) [$RR_{FUCHSONE}=30.5\%$, $RT_{FUCHSONE}=98.4\%$]

An amount of 0.96 g of a 71% aqueous solution of hydrogen peroxide (i.e., 20.0 mmole of pure $H_2O_2$) was introduced over a period of 15 minutes.

After 30 minutes, the results obtained were as follows:

(a) $RT_{HYDROQUINONE/H2}O_2=60.0\%$ (b) $RT_{PYROCATECHIN/H2}O_2=14.0\%$ (c) Ratio $_{HQ/PC}=4.3$

EXAMPLE 58

The procedure of Example 57 was repeated, with the same amount of 70% perchloric acid.

The reaction temperature was also 70° C.

After 28 hours of reaction, the results obtained were as follows:

(a) benzophenone-17.1 g (94 mmole) [$TT_{BENZOPHENONE}=6.0\%$]

(b) fuchsone=1.52 g (5.9 mmole) [$RR_{FUCHSONE}=5.9\%$, $RR_{FUCHSONE}=98\%$]

After cooling, introduced therein was an amount of 0.31 g of a 71% aqueous solution of hydrogen peroxide (i.e., 6.5 mmole of pure $H_2O_2$).

After 15 minutes, the results obtained were as follows:

(a) $RT_{HYDROQUINONE/H2}O_2=53.8\%$ (b) $RT_{PYROCATECHIN/H2}O_2=24.6\%$ (c) Ratio $_{HQ/PC}=2.18$

EXAMPLE 59

The following reagents were introduced into a 100 ml metallic reactor:

(i) 4.7 g (0.050 mole) of phenol, (ii) 9.1 g (0.05 mole) of benzophenone, and (iii) 20 g (1.00 mole) of anhydrous hydrofluoric acid.

The reactor was sealed and the reaction mixture was heated to the selected temperature of 80° C., while being maintained in an agitated condition.

After 4 hours, the reaction mixture was transferred into 100 ml of water; extraction was carried out using dichloromethane. The organic phase obtained was washed with water until it attained a pH of 5. The aqueous and organic phases were separated.

The dichloromethane was evaporated under reduced pressure.

Quantitative analysis was carried out in respect of that medium (11.97 g), providing the following results:

(a) benzophenone-5.82 g (32 mmole) [$TT_{BENZOPHENONE}=36\%$]

(b) diphenylfuchsone=3.97 g (15.4 mmole) [$RR_{FUCHSONE}=30.8$]

This reaction mass was placed into a reactor and 25 mg of 70% by weight perchloric acid were added. The reaction mixture was heated to 30°–35° C. and introduced into same was an amount of 0.802 g of a 71% aqueous solution of hydrogen peroxide (i.e., 16.7 mmole of pure $H_2O_2$).

The reaction temperature increased to 65° C.

After 15 minutes, the results obtained were as follows:

(a') $RR_{HYDROQUINONE/FUCHSONE}$=77.5% and (b') Ratio $_{HQ/PC}$=27

The rate of recovery of the benzophenone was 98.5%.

EXAMPLE 60

The procedure of Example 59 was repeated, except that the reaction medium was diluted 5 times in acetonitrile (acetonitrile/reaction medium ratio by weight=5).

After 15 minutes, the results obtained were as follows:

(a) $RR_{HYDROQUINONE/FUCHSONE}$=82%

(b) Ratio $_{HQ/PC}$=63

The rate of recovery of the benzophenone was 92%.

EXAMPLE 61

The following reagents were introduced into a 100 ml glass round-bottom flask provided with a central agitation system, a condenser, a dropping funnel and a thermometer:

(i) 24 g (0.255 mole) of phenol, (ii) 3.6 g (0.0124 mole) of rosolic acid, and (iii) 25 mg of 70% by weight perchloric acid.

The reaction mixture was heated to the selected reaction temperature of 75° C., while being maintained in an agitated condition at 1,200 rpm.

An amount of 0.0126 mole of hydrogen peroxide in the form of a 70.5% aqueous solution was introduced over a period of 2 minutes via the dropping funnel.

The reaction mixture was then cooled and quantitative analysis of the reaction products was carried out.

After 1 hour, 30 minutes, of reaction, the results obtained were as follows:

(a) $TT_{H2O2}$=100%

(b) $RT_{HYDROQUINONE/H2O2}$=74.5%

(c) $RT_{PYROCATECHIN/H2O2}$=13%

(d) Ratio $_{HQ/PC}$=5.7

EXAMPLE 62

The following reagents were introduced into a glass round-bottom flask as described in Example 1:

(i) 0.828 g (0.003 mole) of carbinol corresponding to diphenylfuchsone, (ii) 8.3 ml of acetonitrile, and (iii) 145.7 mg (0.003 mole) of a 70.5% aqueous solution of hydrogen peroxide.

At the ambient temperature of 25° C., 18 mg (0.12 mmole) of 70% by weight perchloric acid were added.

The reaction temperature autogenously increased to 50° C.

After 15 minutes of reaction, the results obtained were as follows:.

(a) $TT_{H2O2}$=100%

(b) $RR_{HYDROQUINONE/H2O2}$=100%

(c) $RT_{HYDROQUINONE/H2O2}$=100%

The benzophenone was recovered at a recovery rate of 95%.

EXAMPLE 63

The following reagents were introduced into a 100 ml glass round-bottom flask provided with a central agitation system, a condenser, a dropping funnel and a thermometer:

(i) 56.4 g (0.6 mole) of phenol, (ii) 10.92 g (0.06 mole) of benzophenone, and (iii) 46.06 g (0.48 mole) of methanesulfonic acid.

That reaction mixture was heated to 110° C. for a period of 7 hours, while being maintained in an agitated condition at 1,200 rpm.

The reaction mixture was then cooled and 50 ml of water and 100 ml of isopropyl ether were added. The ether phase was decanted and washed 3 times with 50 ml of water.

Quantitative analysis was carried out in respect of that organic ether phase, providing the following results:

(a) FUCHSONE=0.0347 mole (b) BENZOPHENONE=0.0240 mole (e) PHENOL=0.487 mole

That ether phase was transferred into the round-bottom flask indicated above and 0.1 g of perchloric acid was added thereto. The resulting reaction medium was heated to 40° C. and introduced therein over a period of two minutes was an amount of 0.035 mole of hydrogen peroxide in the form of a 70% aqueous solution.

After 1 hour at 45° C., while maintaining agitation at 1,200 rpm, the reaction medium was cooled. Quantitative analysis was carried out in respect of the residual hydrogen peroxide, as well as the diphenols formed, the results obtained being as follows:

(a) $TT_{H2O2}$=100%

(b) $TT_{FUCHSONE}$=100%

(c) $RR_{HYDROQUINONE/H2O2}$=100%

There was no pyrocatechin.

The benzophenone was recovered at a recovery rate of 100%.

EXAMPLE 64

The following reagents were introduced into a 100 ml glass round-bottom flask provided with a central agitation system, a condenser, a dropping funnel and a thermometer:

(i) 23.5 (0.25 mole) of phenol, (ii) 0.015 g (0.001 mole) of 70% by weight perchloric acid, and (iii) 4.3 g (0.0617 mole) of diphenylfuchsone.

The resulting reaction mixture was heated to 75° C. and 0.017 mole of hydrogen peroxide in the form of a 70% aqueous solution was introduced over a period of two minutes via the dropping funnel, while maintaining agitation at 1,200 rpm.

After 30 minutes of reaction the reaction medium was cooled. Quantitative analysis was carried out in respect of the residual hydrogen peroxide by means of iodometry and in respect of the diphenols formed by high-performance liquid chromatography.

The results obtained were as follows:

(a) $TT_{H2O2}$=100%

(b) $RT_{HYDROQUINONE/H2O2}$=93%

(c) $RT_{PYROCATECHIN/H2O2}$=2%

EXAMPLE 65

The following reagents were introduced into the apparatus described in Example 64:

(i) 23.5 g (0.25 mole) of phenol, and (ii) 3.45 g (0.0125 mole) of carbinol corresponding to diphenylfuchsone.

The resulting reaction mixture was heated to a temperature of 65° C. and then 0.607 g (0.0125 mole) of hydrogen peroxide in the form of a 70% aqueous solution was added thereto over a period of 2 minutes via the dropping funnel, while maintaining agitation at 1,200 rpm. The operation was thus not carried out using a strong acid.

After 1 hour, the mixture was cooled and quantitative analysis was carried out in respect of the residual hydrogen peroxide and the products formed.

The results obtained were as follows:

(a) $TT_{H_2O_2}=100\%$ (b) $RT_{HYDROQUINONE/H_2O_2}=45\%$ (c) $RT_{PYROCATECHIN/H_2O_2}=31.5\%$ (d) Ratio $_{HQ/PC}=1.43$

EXAMPLE 66

The following reagents were introduced into an apparatus as described in Example 64:

(i) 23.5 g (0.25 mole) of phenol, (ii) 3.2 g (0.0125 mole) of fuchsone, and (iii) 1.8 g (0.0125 mole) of 70% by weight perchloric acid.

The resulting reaction mixture was heated to a temperature of 75° C. and 0.60 g (0.0125 mole) of hydrogen peroxide was added thereto over a period of two minutes in the form of a 70% by weight aqueous solution, with agitation at 1,200 rpm.

After 15 minutes the reaction medium was cooled and quantitative analysis was carried out in respect of the products formed.

The results obtained were as follows:

(a) $TT_{H_2O_2}=100\%$ (b) $TT_{FUCHSONE}=79\%$ (c) $RT_{HYDROQUINONE/H_2O_2}=80.5\%$ (d) $RT_{PYROCATECHIN/H_2O_2}=12\%$ (e) Ratio $_{HQ/PC}=6.7$

EXAMPLE 67 TO 83

Examples 67 to 83 illustrate the use of a fuchsone as a catalyst for the hydroxylation of a phenolic compound.

In said Examples, the following abbreviations have the following definitions:

$$TT_{H_2O_2} = \frac{\text{number of moles of hydrogen peroxide converted}}{\text{number of moles of hydrogen peroxide introduced}} \%$$

$$RT_{HQ} = \frac{\text{number of moles of hydroquinone formed}}{\text{number of moles of hydrogen peroxide converted}} \%$$

$$RT_{PC} = \frac{\text{number of moles of pyrocatechin formed}}{\text{number of moles of hydrogen peroxide converted}} \%$$

Described below is the operating procedure which was followed in Examples 67 to 83.

The following reagents were introduced into a 100 ml glass round-bottom flask provided with a central agitation system, a condenser, a dropping funnel and a thermometer:

(i) 47 g (0.50 mole) of phenol, and (ii) $\underline{x}$ g of a fuchsone of formula (III) and/or (IV).

An amount of $\underline{y}$ g of strong acid (perchloric acid) and, optionally, $\underline{z}$ g of aprotic solvent were then introduced.

The different amounts ($\underline{x}$, $\underline{y}$ and $\underline{z}$) are reported in the following Tables.

The reaction mixture was heated to the selected reaction temperature of 75° C. (unless otherwise indicated) while being maintained in an agitated condition at 1,200 rpm.

The 70.5% by weight aqueous solution of hydrogen peroxide was introduced over a period of 2 minutes via the dropping funnel, in an amount which is also reported in the following Tables.

The reaction mixture was then cooled and quantitative analysis was carried out in respect of the reaction products. Quantitative analysis of the residual hydrogen peroxide was conducted by iodometry, while quantitative analysis in respect of the diphenols formed was carried out by high-performance liquid chromatography.

EXAMPLES 67 TO 70

These four Examples relate to the hydroxylation of phenol by means of hydrogen peroxide in the presence of perchloric acid and in the absence of organic solvent.

The fuchsone used was diphenyl fuchsone, corresponding to the following formula:

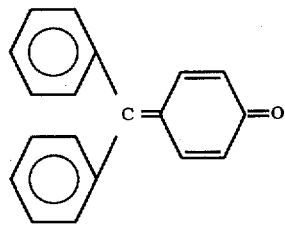

The experiments were carried out in accordance with the operating procedure defined above.

All of the conditions and results obtained are reported in the following Table III:

TABLE III

| | | | Hydroxylation of phenol by means of $H_2O_2$/perchloric acid/diphenylfuchsone: | | | | | | |
|---|---|---|---|---|---|---|---|---|---|
| Example | Fuchsone of formula (III) [Fuchsone/$H_2O_2$ molar ratio] | Organic solvent [organic solvent/ phenol molar ratio] | $H_2O_2$/phenol molar ratio | $H^+/H_2O_2$ molar ratio | Duration | $TT_{H_2O_2}$ | $RT_{HQ}$ | $RT_{PC}$ | Ratio HQ/PC |
| 67 | Diphenylfuchsone 0.240 | without | $5.2 \cdot 10^{-2}$ | $1.1 \cdot 10^{-2}$ | 30 min | 100 | 46.0 | 31.5 | 1.46 |
| 68 | Diphenylfuchsone 0.240 | without | $5.2 \cdot 10^{-2}$ | $1.1 \cdot 10^{-2}$ | 30 min | 100 | 46.0 | 31.5 | 1.46 |
| 69 | Diphenylfuchsone 0.199 | without | $5.25 \cdot 10^{-2}$ | $0.79 \cdot 10^{-2}$ | 60 min | 100 | 47.5 | 34.5 | 1.37 |
| 70 | Diphenylfuchsone 0.100 | without | $5.01 \cdot 10^{-2}$ | $0.84 \cdot 10^{-2}$ | 60 min | 100 | 42.5 | 40.0 | 1.06 |

EXAMPLES 71 AND 72

This series of Examples entailed conducting hydroxylation of the phenol by means of hydrogen peroxide in the presence of perchloric acid and in the absence of organic solvent.

The fuchsone used was rosolic acid, corresponding to the following formula:

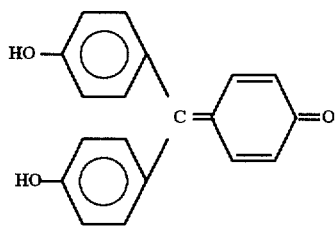

The experiments were carried out in accordance with the operating procedure defined above. All of the conditions and results obtained are reported in the following Table IV:

TABLE IV

Hydroxylation of phenol by means of $H_2O_2$/perchloric acid/rosolic acid:

| Example | Fuchsone of formula (III) [Fuchsone/$H_2O_2$ molar ratio] | Organic solvent [organic solvent/ phenol molar ratio] | $H_2O_2$/phenol molar ratio | $H^+/H_2O_2$ molar ratio | Duration | $TT_{H_2O_2}$ | $RT_{HQ}$ | $RT_{PC}$ | Ratio HQ/PC |
|---|---|---|---|---|---|---|---|---|---|
| 71 | Rosolic acid (0.25) | without | 5.0 | 0.47 | 180 min | 99.5 | 40.0 | 31.5 | 1.27 |
| 72 | Rosolic acid (0.25) | without | 5.0 | 1.15 | 30 min | 100 | 38.0 | 31.0 | 1.22 |

EXAMPLE 73

This Example illustrates the hydroxylation of the phenol by means of hydrogen peroxide in the presence of perchloric acid and a polar organic solvent which was slightly basic such as acetonitrile.

The fuchsone used was the diphenylfuchsone described in Example 67.

The experiment was carried out in accordance with the operating procedure described above.

All of the conditions and results obtained are reported in the following Table V:

TABLE V

Hydroxylation of phenol by means of $H_2O_2$/perchloric acid/diphenylfuchsone:

| Example | Fuchsone of formula (III) [Fuchsone/$H_2O_2$ molar ratio] | Organic solvent [organic solvent/ phenol molar ratio] | $H_2O_2$/phenol molar ratio | $H^+/H_2O_2$ molar ratio | Duration | $TT_{H_2O_2}$ | $RT_{HQ}$ | $RT_{PC}$ | Ratio HQ/PC |
|---|---|---|---|---|---|---|---|---|---|
| 73 | Diphenylfuchsone (0.25) | Acetonitrile (0.50) | $5.1 \cdot 10^{-2}$ | $1.3 \cdot 10^{-2}$ | 180 min | 98.5 | 56.0 | 28.5 | 2.0 |

EXAMPLE 74

This Example illustrates the hydroxylation of phenol by means of hydrogen peroxide in the presence of perchloric acid and an organic solvent which is slightly polar and basic, such as diisopropyl oxide.

The fuchsone used was the diphenylfuchsone defined in Example 67.

The experiment was carried out in accordance with the operating procedure described above.

All the conditions and results obtained are set out in the following Table VI:

TABLE VI

Hydroxylation of phenol by means of $H_2O_2$/perchloric acid/diphenylfuchsone:

| Example | Fuchsone of formula (III) [Fuchsone/$H_2O_2$ molar ratio] | Organic solvent [organic solvent/ phenol molar ratio] | $H_2O_2$/phenol molar ratio | $H^+/H_2O_2$ molar ratio | Duration | $TT_{H_2O_2}$ | $RT_{HQ}$ | $RT_{PC}$ | Ratio HQ/PC |
|---|---|---|---|---|---|---|---|---|---|
| 74 | Diphenylfuchsone (0.25) | Diisopropyl oxide (0.51) | $5.0 \cdot 10^{-2}$ | $1.25 \cdot 10^{-2}$ | 180 min | 99.5 | 39.0 | 25.0 | 1.6 |

EXAMPLE 75

This Example illustrates the procedure of Examples 67 to 70, but with the diphenylfuchsone being replaced by the corresponding carbinol.

All of the conditions and results obtained are reported in the following Table VII:

TABLE VII

Hydroxylation of phenol by means of $H_2O_2$/perchloric acid/diphenylfuchsone carbinol:

| Example | Carbinol of formula (IV) [Carbinol/$H_2O_2$ molar ratio] | Organic solvent [organic solvent/ phenol molar ratio] | $H_2O_2$/phenol molar ratio | $H^+/H_2O_2$ molar ratio | Duration | $TT_{H_2O_2}$ | $RT_{HQ}$ | $RT_{PC}$ | Ratio HQ/PC |
|---|---|---|---|---|---|---|---|---|---|
| 75 | Diphenylfuchsone carbinol (0.245) | without | $5.2 \cdot 10^{-2}$ | $0.37 \cdot 10^{-2}$ | 100 min | 99.0 | 47.0 | 30.0 | 1.57 |

EXAMPLES 76 TO 82

47 g (0.5 mole) of phenol were introduced into a 100 ml glass round-bottom flask provided with a central agitation system, a condenser, a dropping funnel and a thermometer.

Perchloric acid and diphenylfuchsone were then introduced in the amounts reported in Table VIII.

That mixture was heated to 75° C. and a 70% aqueous solution of hydrogen peroxide was introduced over a period of 2 minutes via the dropping funnel, using the amounts indicated in Table VIII and while maintaining agitation at 1,200 rpm.

At the end of the reaction, the reaction mixture was cooled and quantitative analysis of the reaction products was carried The results obtained were as follows:

EXAMPLE 83

The following reagents were introduced into an apparatus as described above:

(i) 47 g (0.5 mole) of phenol,
(ii) 0.61 g (0.00237 mole) of diphenylfuchsone, and
(iii) 0.23 g (0.00237 mole) of 98% sulfuric acid.

The mixture was heated to 75° C. and, while agitating same at 1,200 rpm, 1.21 g (0.0125 mole) of a 70% aqueous solution of hydrogen peroxide was added over a period of two minutes.

After 25 minutes, the mixture was cooled and quantitative analysis of the products formed was carried out.

The results obtained were as follows:

(a) $TT_{H2O2}=100\%$
(b) $RR_{HYDROQUINONE/H2}O_2=35.5\%$
(c) $RR_{PYROCATECHIN/H2}O_2=43\%$
(d) Ratio $_{HQ/PC}=0.82$ While the invention has been described in terms of various preferred embodiments, the skilled artisan will appreciate that various modifications, substitutions, omissions, and changes may be made without departing from the spirit thereof. Accordingly, it is intended that the

TABLE VIII

Hydroxylation of phenol by means of $H_2O_2$/perchloric acid/diphenylfuchsone:

| Example | Fuchsone of formula (III) [Fuchsone/$H_2O_2$ molar ratio] | $H^+/H_2O_2$ molar ratio | $H_2O_2$/phenol molar ratio | Duration | $TT_{H_2O_2}$ | $RT_{HQ}$ | $RT_{PC}$ | Ratio HQ/PC |
|---|---|---|---|---|---|---|---|---|
| 76 | Diphenylfuchsone ($4.65 \cdot 10^{-2}$) | $0.95 \cdot 10^{-2}$ | $5.35 \cdot 10^{-2}$ | 60 min | 99 | 39.5 | 41.5 | 0.95 |
| 77 | Diphenylfuchsone (0.103) | $0.85 \cdot 10^{-2}$ | $5.0 \cdot 10^{-2}$ | 60 min | 100 | 42.5 | 40 | 1.06 |
| 78 | Diphenylfuchsone (0.145) | $0.95 \cdot 10^{-2}$ | $5.2 \cdot 10^{-2}$ | 60 min | 100 | 44.5 | 36 | 1.25 |
| 79 | Diphenylfuchsone (0.199) | $0.80 \cdot 10^{-2}$ | $5.25 \cdot 10^{-2}$ | 60 min | 100 | 48 | 34.5 | 1.38 |
| 80 | Diphenylfuchsone (0.33) | $0.75 \cdot 10^{-2}$ | $5.3 \cdot 10^{-2}$ | 30 min | 100 | 54 | 29 | 1.85 |
| 81 | Diphenylfuchsone (0.57) | $0.89 \cdot 10^{-2}$ | $4.65 \cdot 10^{-2}$ | 30 min | 100 | 68.5 | 18 | 3.85 |
| 82 | Diphenylfuchsone (0.77) | $0.87 \cdot 10^{-2}$ | $4.7 \cdot 10^{-2}$ | 30 min | 100 | 81 | 9 | 9.1 |

What is claimed is:

1. A process for the preparation of a para-dihydroxylated aromatic compound, comprising reacting an oxidizing agent with a p-fuchsone.

2. The process as defined by claim 1, said p-fuchsone having the general formulae (III) and/or (IV):

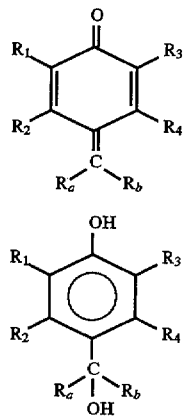

in which $R_a$ and $R_b$, which may be identical or different, are each a hydrocarbon radical having from 3 to 30 carbon atoms, the carbon atoms of each radical $R_a$ and $R_b$ in the α-position with respect to the carbon atom from which they depend being tertiary carbons; and $R_1$, $R_2$, $R_3$ and $R_4$, which may be identical or different, are each a hydrogen atom or an inert substituent, with the proviso that $R_1$ and $R_2$ and/or $R_3$ and $R_4$ borne by two adjacent carbon atoms may together form, with the carbon atoms from which they depend, a ring member.

3. The process as defined by claim 2, wherein formulae (III) and/or (IV), $R_1$, $R_2$, $R_3$ and $R_4$, which may be identical or different, are each a radical $R_O$ selected from among a hydrogen atom, a branched or straight chain alkyl radical having from 1 to 6 carbon atoms, a branched or straight chain alkenyl radical having from 2 to 6 carbon atoms, a branched or straight chain alkoxy radical having from 1 to 6 carbon atoms, an acyl radical having from 2 to 6 carbon atoms, a radical of the following formulae:

—$R_5$—OH
—$R_5$—COOR$_6$
—$R_5$—X
—$R_5$—CF$_3$ wherein $R_5$ is a valence bond or a saturated or unsaturated, branched or straight chain divalent hydrocarbon radical having from 1 to 6 carbon atoms, $R_6$ is a branched or straight chain alkyl radical having from 1 to 6 carbon atoms; and X is a halogen atom; or at least one $R_1$, $R_2$, $R_3$ and $R_4$, which may be identical or different, is a radical $R_7$ selected from among a saturated or unsaturated carbocyclic radical having from 4 to 7 carbon atoms, a radical of the formula:

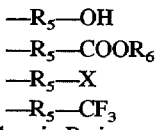

wherein $R_5$ is a valence bond or a saturated or unsaturated, branched or straight chain divalent hydrocarbon radical having from 1 to 6 carbon atoms, $R_O$ is as defined above, and m is an integer ranging from 0 to 4, or a radical —$R_5$—

A—$R_8$ in which $R_5$ is as defined above, $R_8$ is a branched or straight chain alkyl radical having from 1 to 6 carbon atoms or a radical of the formula:

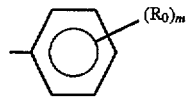

and A is one of the following groups:

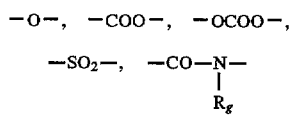

wherein $R_g$ is a hydrogen atom or an alkyl radical having from 1 to 4 carbon atoms, a cyclohexyl or a phenyl radical, with the proviso that $R_1$ and $R_2$ and/or $R_3$ and $R_4$ borne by two adjacent carbon atoms may together form, with the carbon atoms from which they depend, an unsaturated or aromatic carbocycle having from 4 to 7 carton atoms.

4. The process as defined by claim 2, wherein formulae (III) and/or (IV), $R_a$ and $R_b$ are each a branched chain alkyl radical having at least 3 carbon atoms, an aryl radical having at least 6 carbon atoms, or a substituted such radical.

5. The process as defined by claim 1, said p-fuchsone having the general formulae (IIIa) and/or (IVa):

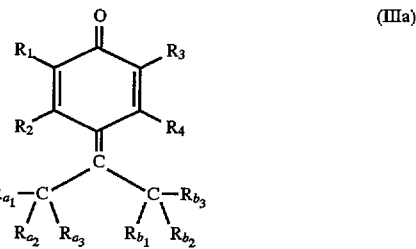

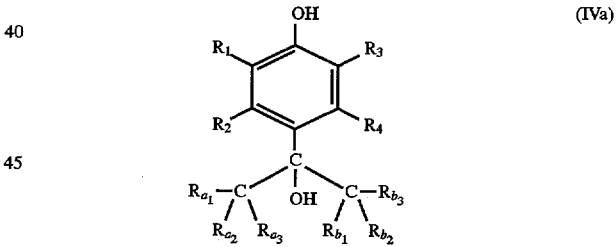

in which $R_{a1}$, $R_{a2}$ and $R_{a3}$ and $R_{b1}$, $R_{b2}$ and $R_{b3}$, which may be identical or different, are each a branched or straight chain alkyl radical having from 1 to 10 carbon atoms, or an optionally substituted cyclohexyl, phenyl or naphthyl radical, with the proviso that $R_{a1}$, $R_{a2}$ and $R_{a3}$ and/or $R_{b1}$, $R_{b2}$ and $R_{b3}$, may together form, with the carbon atom from which they depend, an optionally substituted benzene or naphthalene ring; and $R_1$, $R_2$, $R_3$ and $R_4$, which may be identical or different, are each a hydrogen atom, a branched or straight chain alkyl radical having from 1 to 4 carbon atoms, a branched or straight chain alkoxy radical having from 1 to 4 carbon atoms, a hydroxyl group, a halogen atom, a group —CF$_3$, a cyclohexyl radical, or a phenyl radical, with the proviso that $R_1$ and $R_2$ and/or $R_3$ and $R_4$ borne by two adjacent carbon atoms may together form, with the carbon atoms from which they depend, a benzene ring.

6. The process as defined by claim 5, wherein formulae (IIIa) and/or (IVa), one of the radicals $R_1$, $R_2$, $R_3$ and $R_4$ is a hydroxyl group, a methyl radical, or a methoxy radical, and the other three are hydrogen atoms.

7. The process as defined by claim 1, said p-fuchsone having the formulae (IIIb) and/or (IVb):

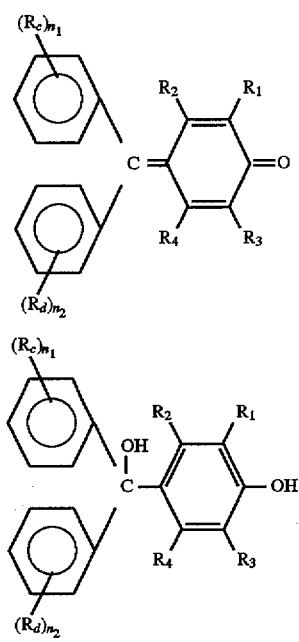

in which $R_1$, $R_2$, $R_3$ and $R_4$, which may be identical or different, are each a hydrogen atom, a branched or straight chain alkyl radical having from 1 to 4 carbon atoms, a branched or straight chain alkoxy radical having from 1 to 4 carbon atoms, a hydroxyl group, a halogen atom, a group —$CF_3$, a cyclohexyl radical, or a phenyl radical, with the proviso that $R_1$ and $R_2$ and/or $R_3$ and $R_4$ borne by two adjacent carbon atoms may together form, with the carbon atoms from which they depend, a benzene ring; $R_c$ and $R_d$, which may be identical or different, are each a hydrogen atom or an inert substituent; and $n_1$ and $n_2$, which may be identical or different, are each a number equal to 0, 1, 2 or 3.

8. The process as defined by claim 7, wherein formulae (IIIb) and/or (IVb), $R_c$ and $R_d$, which may be identical or different, are each a hydrogen atom, a branched or straight chain alkyl radical having from 1 to 4 carbon atoms, a phenyl radical, an alkoxy $R_{10}$—O radical in which $R_{10}$ is a branched or straight chain alkyl radical having from 1 to 4 carbon atoms or a phenyl radical, or a halogen atom.

9. The process as defined by claim 8, wherein formulae (IIIb) and/or (IVb), $R_c$ and $R_d$, which may be identical or different, are in the 4,4'-position, and $n_1$ and $n_2$, which may be identical or different, are each equal to 0 or 1.

10. The process as defined by claim 8, wherein formulae (IIIb) and/or (IVb), $R_c$ and $R_d$, which may be identical or different, are each a hydrogen atom, a methyl, ethyl, tert-butyl or phenyl radical, a methoxy or ethoxy radical, or a hydroxyl group, and are in the 3,3'- or 4,4'-position.

11. The process as defined by claim 1, said oxidizing agent comprising hydrogen peroxide, a peracid, or a hydroperoxide.

12. The process as defined by claim 11, said oxidizing agent comprising an aqueous solution of hydrogen peroxide.

13. The process as defined by claim 12, comprising reacting said p-fuchsone with a stoichiometric amount of hydrogen peroxide.

14. The process as defined by claim 1, carried out in the presence of a catalytically effective amount of a strong acid catalyst.

15. The process as defined by claim 14, said strong acid catalyst comprising sulfuric acid, pyrosulfuric acid, perchloric acid, fluorosulfonic acid, chlorosulfonic acid, trifluoromethanesulfonic acid, methanesulfonic acid, ethanesulfonic acid, ethanedisulfonic acid, benzenesulfonic acid, benzenedisulfonic acid, a toluenesulfonic acid, a naphthalenesulfonic acid, or a naphthalenedisulfonic acid.

16. The process as defined by claim 14, the amount of acid present, expressed by the ratio of the number of equivalents of protons to the number of moles of oxidizing agent, ranging from about $1 \cdot 10^{-4}$ to about 1.0.

17. The process as defined by claim 1, carried out in a reaction solvent comprising a phenolic compound and/or an organic solvent.

18. The process as defined by claim 17, carried out in an organic solvent selected from among an aliphatic or aromatic nitrile, an aliphatic, cycloaliphatic or aromatic ether, a chlorinated aliphatic hydrocarbon, and an alcohol.

19. The process as defined by claim 1, carried out at a temperature ranging from 20° C. to 150° C.

20. The process as defined by claim 1, comprising reacting diphenyl fuchsone, rosolic acid or diphenylmethyl fuchsone with hydrogen peroxide.

21. A process for preparation of a p-dihydroxylated aromatic compound, comprising reacting an oxidizing agent with a p-fuchsone product of the process comprising reacting a phenolic compound having at least one hydrogen atom in the para-position to the hydroxyl function with a non-enolizable ketonic compound, in the presence of a catalytically effective amount of an acid catalyst and, optionally, a cocatalytically effective amount of an ionizable sulfur-containing compound.

22. The process as defined by claim 21, said p-fuchsone product not being isolated from its medium of reaction and directly adding said oxidizing agent thereto.

* * * * *

UNITED STATES PATENT AND TRADEMARK OFFICE
CERTIFICATE OF CORRECTION

PATENT NO. : 5,670,465

DATED : 09/23/97

INVENTOR(S) : Michel Costantini et al.

It is certified that error appears in the above-identified patent and that said Letters Patent is hereby corrected as shown below:

Title page, item [62],

Please correct the Priority Application Number from 5,466,839 to 5,460,839.

Signed and Sealed this

Tenth Day of March, 1998

Attest:

BRUCE LEHMAN

Attesting Officer

Commissioner of Patents and Trademarks